(12) United States Patent
Blume et al.

(10) Patent No.: US 7,683,081 B2
(45) Date of Patent: *Mar. 23, 2010

(54) 1-PHENYL-2-HETEROARYL-SUBSTITUTED BENZIMIDAZOLE DERIVATIVES, THEIR USE FOR THE PRODUCTION OF PHARMACEUTICAL AGENTS AS WELL AS PHARMACEUTICAL PREPARATIONS THAT CONTAIN THESE DERIVATIVES

(75) Inventors: Thorsten Blume, Schildow (DE); Bernd Elger, Berlin (DE); Wolfgang Halfbrodt, Berlin (DE); Joachim Kuhnke, Potsdam (DE); Ursula Moenning, Woltersdorf (DE); Herbert Schneider, Berlin (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 1003 days.

This patent is subject to a terminal disclaimer.

(21) Appl. No.: 11/198,098

(22) Filed: Aug. 4, 2005

(65) Prior Publication Data

US 2005/0267160 A1    Dec. 1, 2005

Related U.S. Application Data

(63) Continuation of application No. 10/366,688, filed on Feb. 14, 2003, now Pat. No. 6,962,932.

(60) Provisional application No. 60/357,834, filed on Feb. 21, 2002.

(30) Foreign Application Priority Data

Feb. 15, 2002  (DE) ................ 102 07 844

(51) Int. Cl.
*A61K 31/4439*   (2006.01)
*A61K 31/4184*   (2006.01)

(52) U.S. Cl. ..................... 514/338; 514/394
(58) Field of Classification Search ............... 514/338, 514/394

See application file for complete search history.

(56) References Cited

U.S. PATENT DOCUMENTS

| 5,552,426 A | 9/1996 | Lunn et al. ............... 514/394 |
| 2002/0006948 A1 | 1/2002 | Halfbrodt et al. |

FOREIGN PATENT DOCUMENTS

| EP | 0694535 | 1/1996 |
| WO | 0151473 | 7/2001 |

OTHER PUBLICATIONS

Thompson et al., Current Medicinal Chemistry, Oct. 2002, 9(19), pp. 1751-1762.*
Brown, Neurology, Jun. 25, 2002, 58(12), pp. 1720-1725.*
Colagiuri et al., American Journal of Public Health, Sep. 2006, vol. 96, No. 9, pp. 1562-1569.*
Park, Diabetes Research and Clinical Practice 66S (2004), S33-S35.*
Curtis et al., The Journal of the American Board of Family Practice, vol. 18, pp. 37-43, (2005).*
Golub et al., Science, vol. 286, Oct. 15, 1999, pp. 531-537.
Thomas et. al., "Minocycline: Neuroprotective Mechanisms in Parkinson's Disease", *Current Pharmaceutical Design*, 2004, vol. 10, 679-686.

* cited by examiner

*Primary Examiner*—Laura L. Stockton
(74) *Attorney, Agent, or Firm*—Millen, White, Zelano, Branigan, P.C.

(57) ABSTRACT

New benzimidazole derivatives are described, their production and their use for the production of pharmaceutical agents for treatment and prevention of diseases that are associated with a microglia activation and T-cell-mediated immunological diseases, as well as pharmaceutical preparations that contain the new benzimidazole derivatives.

21 Claims, No Drawings

1-PHENYL-2-HETEROARYL-SUBSTITUTED BENZIMIDAZOLE DERIVATIVES, THEIR USE FOR THE PRODUCTION OF PHARMACEUTICAL AGENTS AS WELL AS PHARMACEUTICAL PREPARATIONS THAT CONTAIN THESE DERIVATIVES

This application is a continuation of application Ser. No. 10/366,688, filed Feb. 14, 2003, now U.S. Pat. No. 6,962,932.

The invention relates to new benzimidazole derivatives, their production and their use for the production of pharmaceutical agents for treating and preventing diseases that are associated with a microglia activation and of T-cell-mediated immunological diseases, as well as pharmaceutical preparations that contain the new benzimidazole derivatives.

The immune system comprises a considerable number of cells and tissue complexes that mainly communicate with one another via soluble factors. It is known that many immunological diseases are triggered by an imbalance of soluble immune factors, such as, e.g., the cytokines (Mosmann and Coffmann., Ann. Rev. Immunol. 7: 145-173 (1989 Street and Mosmann, FASEB J. 5: 171-177(1991); Lucey et al., Clin. Microbiol. Rev. 4: 532-562 (1996); Powrie and Coffman, Trends Pharmacol. Sci 14: 164-168 (1993); Singh et al., Immunolog. Res., 20: 164-168 (1999)). There are, for example, a considerable number of references to a role of interferon gamma and interleukin 12 in the pathogenesis of autoimmune diseases. Especially to be cited are diseases that are characterized by a T-cell-mediated inflammatory reaction, such as multiple sclerosis, diabetes, chronic inflammatory intestinal diseases (inflammatory bowel diseases). The cytokine interleukin 12 (IL 12) is produced from phagocytic cells, such as macrophages/monocytes, dendrites, B cells and other antigen-presenting cells (APC) and influences both the function of natural killer cells (NK cells) and those of T-lymphocytes. In both cell types, IL 12 can stimulate the production of interferon gamma (IFNγ). T-Lymphocytes can be divided roughly into two categories that are characterized by the expression of certain surface antigens (CD4 and CD8): CD4-positive T cells (helper T cells) and CD8-positive T cells (cytotoxic T cells). The CD4 cells can in turn be divided into T-helper cells 1 (Th1) and T-helper cells 2 (Th2). Especially the Th1-mediated immunological responses are associated with the pathogenesis of numerous immune diseases, especially the autoimmune diseases, such as, e.g.: type I insulin-dependent diabetes mellitus (IDDM), multiple sclerosis, allergic contact dermatitis, psoriasis, rheumatoid arthritis, chronic inflammatory intestinal diseases ("inflammatory bowel diseases"—Crohn's disease, colitis ulcerosa), lupus diseases and other collagenoses as well as acute rejection reactions in allografts ("host-versus-graft"—allograft rejection, "graft-versus-host disease").

Of interleukin 12, it is known that it plays a critical role in the regulation of the Th1 response. In these cells, interleukin 12 induces the production of mainly IL-2, IFNγ, TNFα and TNFβ (Mosmann and Sad, Immunol. Today 17: 138-146 (1996): Gately et al., Annu. Rev. Immunol. 16: 495-521 (1998)). Especially IFNγ is a potent mediator of the IL-12 action. An over-production of interferon gamma can be responsible for, for example, the MHC II (Major Histocompatibility Complex)-associated autoimmune diseases. (In addition, there is also sufficient evidence with respect to a pathological role of interferon gamma in allergic diseases as well as sarcoidosis and psoriasis (Billiau, A., Adv. Immunol., 62: 61-130 (1996); Basham et al. J. Immunol. 130: 1492-1494 (1983); Hu et al., Immunology, 98: 379-385 (1999); Seery, J. P., Arthritis Res., 2: 437-440 (2000)). Moreover, IL-12 and IL-12/IL-18-induced IFNγ from NK cells are essentially involved in the pathomechanism of non-T-cell-mediated inflammation reactions (e.g., "Toxic Shock Syndrome," endotoxemia, sepsis and septic shock, ARDS, "first dose response" in the case of antibody therapy, e.g., OKT3 administration in the case of allografts) (Kum et al., Infect Immun. 69: 7544-7549 (2001); Arad et al., J Leukoc. Biol. 69: 921-927 (2001); Hultgren et al., Arthritis Res. 3: 41-47 (2001), Arndt et al., Am. J. Respir. Cell. Mol. Biol 22: 708-713 (2000); Grohmann et al., J. Immunol. 164: 4197-4203 (2000); Muraille et al., Int. Immunol. 11: 1403-1410 (1999)). IL-12 also plays a role in inflammations with pathomechanisms that are unclear at this time (e.g., eclampsia) (Hayakawa et al., J. Reprod. Immunol. 47: 121-138 (2000); Daniel et al., Am. J. Reprod. Immunol. 39: 376-380 (1998)).

In addition to interleukin 12 and IFNγ, still other cytokines are ascribed a role in the pathogenesis of immune diseases and systemic inflammation reactions, such as, for example, the TNFα. TNFα plays an important pathological role in the case of infectious diseases (such as sepsis, "toxic shock syndrome" (Tracey et al., Nature 330: 662-664 (1987); Basger et al., Circ. Shock, 27: 51-61 (1989); Hinshaw et al., Circ. Shock, 30: 279-292 (1990); Waage, A., Lancet, 351: 603 (1998); Cohen et al., Lancet, 351: 1731 (1998)), but also numerous other immune-mediated diseases.

For the treatment of IL 12-mediated diseases and for the reduction of acute symptoms of these diseases, corticosteroids are frequently used, whose side effects especially in long-term treatment often result in a termination of treatment.

The activation of microglia represents a central step in the inflammation process of almost all degenerative diseases of the central nervous system. The microglia can remain in the activated state over an extended period, in which they produce and secrete various inflammation factors, e.g., reactive oxygen/nitrogen intermediate compounds, proteases, cytokines, complement factors and neurotoxins. The latter in turn produce neuronal dysfunction and degeneration. The activation of microglia can be carried out by various stimuli such as, e.g., Aβ-peptide (β-amyloid, Araujo, D. M. and Cotman, C. M., Brain Res. 569: 141-145 (1992)), prion protein, cytokines or by cell fragments (Combs, C. K. et al., J. Neurosci. 19: 928-939 (1999); Wood, P. L., Neuroinflammation: Mechanisms and Management, Humana Press (1998).

Benzimidazoles that inhibit the activation of microglia after stimulation with the Aβ-peptide are described in WO 01/51473. From this, it is also known that benzimidazoles that inhibit the activation of microglia are used for treatment of neuroinflammatory diseases, such as AIDS dementia, amyotrophic lateral sclerosis, Creutzfeldt-Jakob disease, Down's Syndrome, diffuse Lewy Body disease, Huntington's disease, leukencephalopathy, multiple sclerosis, Parkinson's disease, Pick's disease, Alzheimer's disease, stroke, temporary lobe epilepsy and of tumors.

EP 0 104 727 A1 describes benzimidazole derivatives that are not substituted in 1-position and that have an alkyl group in 2-position. Substituents in the benzene ring of the derivatives are, i.a., pyridyloxy, pyridylalkyl, pyridylalkyoxy and pyridyloxyalkanediyl radicals.

WO 01/21634 A1 also describes benzimidazole derivatives that can be substituted in 1-position with an alkanediylamido group, in 2-position with, i.a., a substituted phenyl or heteroaryl radical, and in the anellated benzene ring with, i.a., at least one substituted alkoxy, alkylamino, alkylsulfonyl and alkylsulfoxide radical. It is indicated that these substances can be used for a considerable number of possible indications as active ingredients in pharmaceutical agent preparations.

In U.S. Pat. No. 5,552,426, substituted benzimidazoles are indicated that have, i.a., a phenyl or naphthyl radical in 1-position and, i.a., a phenyl or heterocyclic radical in 2-position. The anellated benzene ring of the benzimidazoles is preferably substituted with an alkoxy or aminoalkoxy radical. An effectiveness against diseases that are based on a neurotoxicity that is associated with a β-amyloid peptide is ascribed to such compounds.

WO 97/12613 A1 describes various inflammation-inhibiting and arteriosclerosis-preventing agents. For example, benzimidazole derivatives are indicated as active ingredients that are substituted in 1-position with, i.a., a phenyl radical or substituted phenyl radical, and in 2-position with an alkoxy radical. Substituents in the benzene ring of the active ingredient compounds can be, i.a., alkyl, nitro, halo, alkoxy, amino, ester, amide, alkanediylalkoxy and alkanediylamino radicals.

In EP 0 520 200 A2, benzimidazole derivatives are indicated that have aryl radicals that are substituted in 1-position and amino groups that are monosubstituted or disubstituted in 2-position or are unsubstituted. The benzene ring of the benzimidazole skeleton can be substituted with halogen, trifluoromethyl and/or cyano. These compounds are used for treating diseases that are associated with an increased activation of Ca-channels.

In WO 97/33873 A1, benzimidazole derivatives are also indicated that are used for treating cystitis. In 1-position, these compounds can have, i.a., phenyl, naphthyl and unsaturated heterocyclic radicals. In 2-position, the derivatives can be substituted with alkoxy, phenylalkoxy, naphthylalkoxy, heterocyclic alkoxy or unsaturated heterocyclic alkoxy radicals. The benzene ring of the skeleton of the derivatives can be substituted with nitro, alkanoyl, amino, alkyl, alkoxy, cycloalkyl, heterocyclic, unsaturated heterocyclic, halo, alkylthio, hydroxyalkylidenyl, hydroxyalkylidenylamino, aminoalkylidenyl, aminoalkoxy, hydroxyalkyl, heterocyclic alkoxy, aminoalkylidenyl or trifluoromethyl radicals.

In EP 0 531 883 A1, condensed 5-membered heterocycles are indicated, for example substituted benzimidazole derivatives, whereby these compounds, according to the general description of the compounds, are preferably substituted with a substituted alkyl radical in 1-position and, for example, with an O-alkanediyl, S-alkanediyl, NH-alkanediyl, N(alkyl)-alkanediyl, SO-alkanediyl or SO$_2$-alkanediyl radical in 2-position. The described compounds are to have an antithrombic action.

For a possible therapy of neuroinflammation, to date non-steroidal inflammation inhibitors (COX II inhibitors) [McGeer, P. L., Roger, *Neurology,* 42, 447-449 (1992), Rogers, J.; Kirby, L. C.; Hempleman, S. R.; Berry, D. L.; McGeer, P. L.; Kaszniak, A. W.; Zalinski, J.; Cofield, M.; Mansukhani, L.; Wilson, P.; Kogan, F., *Neurology,* 43, 1609-1611 (1993), Andersen, K.; Launer, L. J.; Ott, A.; Hoes, A. W.; Breteler, M. M. B.; Hofman, A., *Neurology,* 45, 1441-1445 (1995), Breitner, J. C. S.; Gau, B. A.; Welsh, K. A.; Plassman, B. L.; McDonald, W. M.; Helms, M. J.; Anthony, J. C., *Neurology,* 44, 227-232 (1994), The Canadian Study of Health and Aging, *Neurology,* 44, 2073-2079 (1994)], Cytokine Modulators [McGeer, P. L.; McGeer, E. G., *Brain Res. Rev.,* 21: 195-218 (1995), McGeer, E. G.; McGeer, P. L., *CNS Drugs* 7, 214-228 (1997), Barone, F. C. and Feuerstein, G. Z., *J. Cerebral Blood Flow and Metabolism,* 19, 819-834 (1999)] and complementary cascade inhibitors [Chen, S., Frederickson, R. C. A., and Brunden, K. R., *Neurobiol. Aging* (1996), McGeer, E. G.; McGeer, P. L., *Drugs,* 55: 739-746 (1998)] have been described.

The compounds that are known for treating immunological diseases, such as, e.g., steroids, frequently act on several factors in the immune system and thus trigger numerous side effects. The object is therefore to make available substances that inhibit the cytokine activity based on their microglia activity without triggering serious toxic side effects.

The problem is solved by novel benzimidazole derivatives according to claim 1, in addition by the use of a benzimidazole derivative according to the invention for the production of a pharmaceutical agent for interrupting the IL 12 and INFγ production in cells of monocytic origin or T cells and NK cells.

Based on their ability to interrupt the production of IL 12 and TNFα in monocytes/macrophages/dendrites and the IFNγ production in T cells and NK cells, microglia inhibitors are suitable for treating numerous diseases that are triggered by the increase production of cytokines, such as, e.g., TNFα, β, IFNγ, IL-2 and IL 12, such as inflammatory diseases that are not based on neuroinflammation, autoimmune diseases, allergic and infectious diseases, toxin-induced inflammations, pharmacologically triggered inflammation reactions as well as pathophysiologically relevant inflammation reactions of an origin that is unclear at this time.

The benzimidazole derivatives according to the invention have the following general structural formula I:

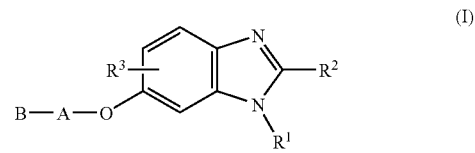

Here:

$R^1$ is a phenyl group that is optionally substituted with up to three of the following substituents, independently of one another:
F, Cl, Br, I
OH, $OR^4$, $OCOR^4$
$SR^4$, $SOR^4$, $SO_2R^4$,
$R^4$,
$NH_2$, $NHR^4$, $NR^4R^{4'}$
or two adjacent substituents at $R^1$ together form an
—O—CH$_2$—O—, —O—CH$_2$—CH$_2$—O— or
—CH$_2$—CH$_2$—CH$_2$ group, $R^2$ is a monocyclic or bicyclic 5- to 10-membered heteroaryl group with 1-2 heteroatoms, selected from N, S and O, which optionally is substituted with up to two of the following substituents, independently of one another:
F, Cl, Br, I
OH, $OR^4$, $OCOR^4$,
$COR^4$,
$SR^4$, $SOR^4$, SO2$R^4$,
$R^4$,
or two adjacent substituents at $R^2$ together form an
—O—CH$_2$—O—, —O—CH$_2$—CH$_2$—O— or
—CH$_2$—CH$_2$—CH$_2$— group, $R^3$ is H, OH or O—C$_{1-6}$-alkyl, $R^4$ and $R^{4'}$, independently of one another, are C$_{1-4}$-perfluoroalkyl or C$_{1-6}$-alkyl, A is a C$_{2-6}$-alkylene group, which optionally is substituted with =O, OH, O—C$_{1-3}$-alkyl, NH$_2$, NH—C$_{1-3}$-alkyl, NH—C$_{1-3}$-alkanoyl, N(C$_{1-3}$-alkyl)$_2$, and N(C$_{1-3}$-alkyl)(C$_{1-3}$-alkanoyl), B is COOH, CONH$_2$, CONHNH$_2$, CONHR$^5$, CONR$^5$R$^{5'}$,
  in each case bonded to a carbon atom of group A,
R$^5$ and R$^{5'}$, independently of one another, are in each case
  a radical, selected from the group that comprises C$_{1-6}$-alkyl, C$_{2-6}$-alkenyl, C$_{2-6}$-alkinyl, whereby a C atom can be exchanged for O, S, SO, SO$_2$, NH, N—C$_{1-3}$-alkyl or N—C$_{1-3}$-alkanoyl, and also (C$_{0-3}$-alkanediyl-C$_{3-7}$-cycloalkyl), whereby in a five-membered cycloalkyl ring, a ring member can be ring N or ring O, and in a six- or seven-membered cycloalkyl ring, one or two ring members in each case can be ring-N atoms and/or ring-O atoms, whereby the ring-N atoms optionally can be substituted with C$_{1-3}$-alkyl or C$_{1-3}$-alkanoyl, as well as also (C$_{0-3}$-alkanediyl-phenyl) and (C$_{0-3}$-alkanediyl-heteroaryl), whereby the heteroaryl group is five- or six-membered and contains one or two heteroatoms that are selected from the group that comprises N, S and O,
  whereby all above-mentioned alkyl and cycloalkyl radicals optionally can be substituted with up to two radicals that are selected from the group that comprises CF$_3$, C$_2$F$_5$, OH, O—C$_{1-3}$-alkyl, NH$_2$, NH—C$_{1-3}$-alkyl, NH—C$_{1-3}$-alkanoyl, N(C$_{1-3}$-alkyl)$_2$, N(C$_{1-3}$-alkyl)(C$_{1-3}$-alkanoyl), COOH, CONH$_2$ and COO—C$_{1-3}$-alkyl, and all above-mentioned phenyl and heteroaryl groups optionally can be substituted with up to two radicals that are selected from the group that comprises F, Cl, Br, CH$_3$, C$_2$H$_5$, OH, OCH$_3$, OC$_2$H$_5$, NO$_2$, N(CH$_3$)$_2$, CF$_3$, C$_2$F$_5$ and SO$_2$NH$_2$
  or R$^5$ and R$^{5'}$ together with the N atom form a five- to seven-membered heterocyclic ring that can contain another N or O or S atom and that can be substituted with C$_{1-4}$-alkyl, (CO$_{0-2}$-alkanediyl-C$_{1-4}$-alkoxy), C$_{1-4}$-alkoxycarbonyl, aminocarbonyl or phenyl as well as their optical or geometric isomers or tautomeric forms or pharmaceutically applicable salts, whereby the following compounds are ruled out:
6-[[1-Phenyl-2-(pyridin-4-yl)-1H-benzimidazol-6-yl]oxy]hexanoic acid,
6-[[1-phenyl-2-(benzothien-2-yl)-1H-benzimidazol-6-yl]oxy]hexanoic acid.
Preferred are compounds in which
  R$^1$ is a phenyl group, which optionally is substituted with up to two of the following substituents, independently of one another:
    F, Cl,
    OH, OR$^4$, OCOR$^4$
    SR$^4$,
    R$^4$ or
    two adjacent substituents at R$^1$ form an —O—CH$_2$—O— or —CH$_2$—CH$_2$—CH$_2$— group.
Preferred are also benzimidazole derivatives, in which
  R$^2$ is a monocyclic 5- to 6-membered heteroaryl group with 1-2 heteroatoms, selected from the group that comprises N, S and O, which optionally is independently substituted with up to two of the following substituents:
    F, Cl,
    OR$^4$, OCOR$^4$
    SR$^4$, SOR$^4$, SO$_2$R$^4$,
    R$^4$ or
    two adjacent substituents at R$^2$ form an —O—CH$_2$—O— or —CH$_2$—CH$_2$—CH$_2$— group.
Preferred are also benzimidazole derivatives in which
  R$^3$ is H.
Preferred are also benzimidazole derivatives in which
  R$^4$ and R$^{4'}$, independently of one another, are C$_{1-2}$ perfluoroalkyl, and C$_{1-4}$ alkyl.

Preferred are also benzimidazole derivatives in which
  R$^5$ and R$^{5'}$, independently of one another, are C$_{1-6}$ alkyl, whereby a carbon atom can be exchanged for O, S, SO, SO$^2$, C$_{3-5}$ cycloalkyl-C$_{0-3}$ alkylene, whereby in a 5-membered cycloalkyl ring, a ring member can be an N or an O, whereby the ring nitrogen optionally is substituted with C$_{1-3}$ alkyl or C$_{1-3}$ alkanoyl,
  C$_{0-2}$ alkylene-(5- to 6-membered heteroaryl with 1-2 heteroatoms from N, S and O)
  whereby all above-mentioned alkyl and cycloalkyl radicals can be substituted with CF$_3$, OH, NH2, NHC$_{1-3}$ alkyl, NHC$_{1-3}$ alkanoyl, N(C$_{1-3}$alkyl)$_2$, N(C$_{1-3}$ alkyl)(C$_{1-3}$ alkanoyl), COOH, CONH$_2$ and all above-mentioned heteroaryl groups with one or two substituents from the group that consists of F, Cl, CH$_3$, C$_2$H$_5$, OCH$_3$, OC$_2$H$_5$, CF$_3$, C$_2$F$_5$, or R$^5$ and R$^{5'}$ together with the nitrogen atom form a 5- to 7-membered heterocyclic compound, which can contain another oxygen, nitrogen or sulfur atom and can be substituted with C$_{1-4}$-alkyl or C$_{1-4}$-alkoxy-C$_{0-2}$-alkyl.
Preferred are benzimidazole derivatives in which
  A is a straight-chain C$_{3-6}$-alkylene.
Preferred are benzimidazole derivatives in which
  B is COOH or CONH$_2$
    in each case bonded to a carbon atom of group A.
Especially preferred are the following benzimidazoles:
6-[[1-(4-Methylphenyl)-2-(3-pyridinyl)-1H-benzimidazol-6-yl]oxy]hexanoic acid
5-[[1-(4-methylphenyl)-2-(3-pyridinyl)-1H-benzimidazol-6-yl]oxy]pentanoic acid
4-[[1-(4-methylphenyl)-2-(3-pyridinyl)-1H-benzimidazol-6-yl]oxy]butyric acid
6-[[1-(4-methylphenyl)-2-(4-pyridinyl)-1H-benzimidazol-6-yl]oxy]hexanoic acid
6-[[1-(4-methylphenyl)-2-(3-thienyl)-1H-benzimidazol-6-yl]oxy]hexanoic acid
5-[[1-(4-methylphenyl)-2-(3-thienyl)-1H-benzimidazol-6-yl]oxy]pentanoic acid
4-[[1-(4-methylphenyl)-2-(3-thienyl)-1H-benzimidazol-6-yl]oxy]butyric acid
5-[[1-phenyl-2-(3-thienyl)-1H-benzimidazol-6-yl]oxy]pentanoic acid
4-[[1-phenyl-2-(3-thienyl)-1H-benzimidazol-6-yl]oxy]butyric acid
6-[[1-phenyl-2-(3-thienyl)-1H-benzimidazol-6-yl]oxy]hexanoic acid
6-[[1-(4-fluorophenyl)-2-(3-thienyl)-1H-benzimidazol-6-yl]oxy]hexanoic acid
5-[[1-(4-fluorophenyl)-2-(3-thienyl)-1H-benzimidazol-6-yl]oxy]pentanoic acid
6-[[1-(4-fluorophenyl)-2-(3-pyridinyl)-1H-benzimidazol-6-yl]oxy]hexanoic acid
5-[[1-(4-fluorophenyl)-2-(3-pyridinyl)-1H-benzimidazol-6-yl]oxy]pentanoic acid
5-[[1-phenyl-2-(3-pyridinyl)-1H-benzimidazol-6-yl]oxy]pentanoic acid
4-[[1-phenyl-2-(3-pyridinyl)-1H-benzimidazol-6-yl]oxy]butyric acid
6-[[1-phenyl-2-(3-pyridinyl)-1H-benzimidazol-6-yl]oxy]hexanoic acid
N-(3-methoxypropyl)-6-[[1-(4-methylphenyl)-2-(3-pyridinyl)-1H-benzimidazol-6-yl]oxy]hexanamide
6-[[1-(4-methylphenyl)-2-(3-pyridinyl)-1H-benzimidazol-6-yl]oxy]-1-morpholin-1-ylhexan-1-one
N-methyl-6-[[1-(4-methylphenyl)-2-(3-pyridinyl)-1H-benzimidazol-6-yl]oxy]hexanamide N,N-dimethyl-6-[[1-(4-methylphenyl)-2-(3-pyridinyl)-1H-benzimidazol-6-yl]oxy]hexanamide
6-[[1-(4-methylphenyl)-2-(3-pyridinyl)-1H-benzimidazol-6-yl]oxy]hexanamide
N-cyclopropyl-6-[[1-(4-methylphenyl)-2-(3-thienyl)-1H-benzimidazol-6-yl]oxy]hexanamide
N-methyl-6-[[1-(4-methylphenyl-2-(3-thienyl)-1H-benzimidazol-6-yl]oxy]hexanamide
6-[[1-(4-methylphenyl)-2-phenyl-1H-benzimidazol-6-yl]oxy]-1-(thiazolidin-3-yl)-hexan-1-one
N-(2-methoxyethyl)-5-[[1-(4-methylphenyl)-2-(3-pyridinyl)-1H-benzimidazol-6-yl]oxy]pentanamide
N,N-dimethyl-5-[[1-(4-methyphenyl)-2-(3-pyridinyl)-1H-benzimidazol-6-yl]oxy]-pentanamide
5-[[1-(4-methylphenyl)-2-(3-pyridinyl)-1H-benzimidazol-6-yl]oxy]pentanamide
6-[[1-(4-methylphenyl)-2-(2-thienyl)-1H-benzimidazol-6-yl]oxy]hexanoic acid.

This invention comprises the physiologically compatible salts of the above-mentioned compounds, especially the acid salts of the nitrogen bases of the benzimidazole derivatives according to the invention, also the salts of carboxylic acids of the derivatives according to the invention with bases.

The benzimidazole derivatives according to the invention can have one or more asymmetric centers, such that the compounds can occur in several isomeric forms. The compounds of formula I can also be present as tautomers, stereoisomers or geometric isomers. The invention also comprises all possible isomers, such as E- and Z-isomers, S- and R-enantiomers, diastereomers, racemates and mixtures thereof including the tautomeric compounds. All of these isomeric compounds are—even if not expressly indicated otherwise in each case—components of this invention.

The isomer mixtures can be separated into enantiomers or E/Z-isomers according to commonly used methods, such as, for example crystallization, chromatography or salt formation.

The heteroaryl groups that are contained in the benzimidazole compounds according to the invention are built up of five or ten skeleton atoms and can contain one or two heteroatoms. Heteroatoms are oxygen (O), nitrogen (N) and sulfur (S).

Examples of monocyclic heteroaryl groups are pyrrolyl, thienyl, furanyl, imidazolyl, thiazolyl, isothiazolyl, oxazolyl, isoxazolyl, pyrazolyl, pyridyl, pyrimidinyl, pyrazinyl and pyridazinyl.

Examples of a bicyclic heteroaryl group are indolyl, isoindolyl, benzothiophenyl, benzofuranyl, benzimidazolyl, indazolyl, quinolyl, isoquinolyl, phthalazinyl, quinazolinyl, cinnolinyl, quinoxalinyl and naphthyridinyl. If the heteroaryl group is part of $R^1$, the binding to N of the benzimidazole is carried out via a carbon atom.

Heteroaryl radicals can be bonded in any way to the benzimidazole skeleton or another group, for example as 2-, 3- or 4-pyridinyl, as 2- or 3-thienyl or as 1-imidazolyl.

Alkyl groups can be straight-chain or branched. Examples of alkyl groups are methyl, ethyl, n-propyl, iso-propyl, n-butyl, sec-butyl, tert-butyl, n-pentyl, sec-pentyl, tert-pentyl, neo-pentyl, n-hexyl, and sec-hexyl.

Perfluorinated alkyls are preferably $CF_3$ and $C_2F_5$.

Cycloalkyl groups are preferably defined in each case as cyclopropyl, cyclobutyl, cyclopentyl, cyclohexyl or cycloheptyl.

Mentioned as a saturated heterocyclic ring or as a cycloalkyl with one or more heteroatoms are, for example: piperidine, pyrrolidine, tetrahydrofuran, morpholine, piperazine, hexahydroazepine as well as 2,6-dimethyl-morpholine, N-phenyl-piperazine, 2-methoxymethyl-pyrrolidine, piperidine-4-carbonamide, thiomorpholine and thiazolidine, whereby the linkage can be carried out via optionally present ring-N atoms.

As straight-chain or branched alkylene for A with up to six C atoms, there can be mentioned, for example: ethylene, propylene, butylene, pentylene, hexylene, also 1-methylethylene, 1-ethylethylene, 1-methylpropylene, 2-methylpropylene, 1-methyl-butylene, 2-methylbutylene, 1-ethylbutylene, 2-ethylbutylene, 1-methylpentylene, 2-methylpentylene, 3-methylpentylene as well as analogous compounds.

A can be substituted in two places, preferably in one place, with OH, $NH_2$, NH—$C_{1-3}$-alkyl or NH—$C_{1-3}$-alkanoyl.

The physiologically compatible acid salts of the nitrogen bases of the benzimidazole derivatives according to the invention can be formed with inorganic and organic acids, for example with oxalic acid, lactic acid, citric acid, fumaric acid, acetic acid, maleic acid, tartaric acid, phosphoric acid, hydrochloric acid, hydrobromic acid, sulfuric acid, p-toluenesulfonic acid and methanesulfonic acid.

For salt formation of acid groups, especially carboxylic acid groups, the inorganic or organic bases that are known for forming physiologically compatible salts, such as, for example, alkali hydroxides, especially sodium hydroxide and potassium hydroxide, alkaline-earth hydroxides, such as calcium hydroxide, also ammonia, as well as amines, such as ethanolamine, diethanolamine, triethanolamine, N-methylglucamine and tris-(hydroxymethyl)-methylamine, are also suitable.

The compounds of formula I inhibit the activation of the microglia and the production of interleukin 12 (IL 12) and interferon γ (IFNγ) The invention therefore also relates to the use of a compound of formula I, as well as optical or geometric isomers thereof or tautomers thereof or physiologically compatible salts for the production of a pharmaceutical agent for treating or preventing a disease that is associated with a microglia activation, especially a disease that is triggered by the overproduction of IL 12 and IFNγ and for induction of interleukin 10 (IL-10).

In a preferred embodiment, the compounds according to the invention are used for treating a T-cell-mediated, especially a Th1-cell-mediated immunological disease and non-T-cell-mediated inflammation reactions. In particular, the compounds according to the invention are used for the production of a pharmaceutical agent for interrupting the IL 12 and IFNγ production in cells of monocytic origin or T cells and NK cells. Based on their ability to interrupt the production of IL 12 and TNFα in monocytes/macrophages and the IFNγ production in T cells, the compounds according to the invention are suitable for treating numerous diseases that are triggered by the increased production of cytokines, such as, e.g., TNFα, β, IFNγ, IL 2 and IL 12, such as inflammatory diseases that are not based on neuroinflammation, autoimmune diseases, allergic and infectious diseases, toxin-induced inflammations, pharmacologically triggered inflammation reactions as well as pathophysiologically relevant inflammation reactions of an origin that is unclear at this time.

Examples of inflammatory and autoimmune diseases are: chronic inflammatory intestinal diseases (inflammatory bowel diseases, Crohn's disease, ulcerative colitis), arthritis, allergic contact dermatitis, psoriasis, pemphigus, asthma, multiple sclerosis, diabetes, type-1 insulin-dependent diabetes mellitus, rheumatoid arthritis, lupus diseases and other collagenoses, Graves' disease, Hashimoto's disease, "graft-versus-host disease" and transplant rejection.

Examples of allergic, infectious and toxin-triggered and ischemia-triggered diseases are: sarcoidosis, asthma, hypersensitive pneumonitis, sepsis, septic shock, endotoxin shock, toxic shock syndrome, toxic liver failure, ARDS (acute respiratory distress syndrome), eclampsia, cachexia, acute virus infections (e.g., mononucleosis, fulminating hepatitis), and post-reperfusion organ damage.

An example of a pharmacologically triggered inflammation with pathophysiological relevance is the "first dose response" after the administration of anti-T-cell antibodies such as OKT3.

An example of systemic inflammation reactions of an origin that is unclear at this time is eclampsia.

Examples of neuroinflammatory diseases that are associated with a microglia activation are AIDS dementia, amyotrophic lateral sclerosis, Creutzfeldt-Jakob disease, Down's Syndrome, diffuse Lewy Body disease, Huntington's disease, leukencephalopathy, multiple sclerosis, Parkinson's disease, Pick's disease, Alzheimer's disease, stroke, temporary lobe epilepsy and tumors. The invention therefore also relates to the use of the indicated benzimidazole derivatives for treating these diseases as well as for preventing these diseases.

Compounds that with stimulation with the Aβ-peptide achieve an inhibition of the microglia activity of at least 20% and an inhibition of the cytokine activity of at least, 30% are suitable, according to the invention, as microglia inhibitors. The biological properties of the microglia inhibitors can be shown according to the methods that are known to one skilled in the art, for example with the aid of the testing methods that are described below and in WO 01/51473.

Example 29 describes how the inhibition of the microglia activation can be measured. In this case, the microglia can be activated by various stimuli such as, for example, with Aβ-peptide [β-amyloid, Araujo, D. M. and Cotman, C. M., *Brain Res.* 569: 141-145 (1992)], with prion protein, cytokines or by cell fragments [Combs, C. K. et al., *J. Neurosci.* 19: 928-939, (1999); Wood, P. L., Neuroinflammation: Mechanisms and Management, *Humana Press*, (1998)].

The stimulation with the Aβ-peptide corresponds to the pathophysiological situation in the case of Alzheimer's disease. In this test, the substances according to the invention in the case of stimulation with the Aβ-peptide showed an inhibition of the microglia activation. The inhibition of the microglia activation by the substances according to the invention results in a strong reduction of the cytokine production and cytokine secretion, for example of Il1β and TNFβ (measured by ELISA and mRNA expression analysis), and in a reduced secretion of reactive oxygen/nitrogen intermediate compounds. Several inflammation factors are thus equally inhibited.

The in vivo action of the substances according to the invention was shown in an MCAO model in rats. This model simulates the condition of a stroke. The substances according to the invention reduce the microglia activation, which occurs in the case of acute brain lesions in the brains of animals.

The inhibition of cytokine production is produced, for example, by measuring TNFα and interleukin 12 in lipopolysaccharide (LPS)-stimulated THP-1 cells.

The compounds according to the invention inhibit the TNFα and interleukin 12 production in lipopolysaccharide (LPS)-stimulated THP-1 cells. To visualize the influence of substances on the T-cell activation, for example, the measurement of the INFγ secretion is used. The compounds according to the invention inhibit the INFγ production of peripheral mononuclear blood cells.

The invention also relates to pharmaceutical agents that contain one or more compounds of general formula I according to the invention as well as one or more vehicles. The pharmaceutical agents or compositions of the invention are produced with commonly used solid or liquid vehicles or diluents and commonly used pharmaceutical and technical adjuvants according to the desired method of administration with a suitable dosage in a way that is known in the art. Preferred preparations consist in a dispensing form that is suitable for oral, enteral or parenteral administration, for example i.p. (intraperitoneal), i.v. (intravenous), i.m. (intramuscular) or percutaneous administration. Such dispensing forms are, for example, tablets, film tablets, coated tablets, pills, capsules, powders, creams, ointments, lotions, liquids, such as syrups, gels, injectable liquids, for example for i.p., i.v., i.m. or percutaneous injection, etc. In addition, depot forms such as implantable preparations, as well as suppositories, are also suitable. In this case, depending on their type, the individual preparations release to the body the derivatives according to the invention gradually or all at once in a short time.

For oral administration, capsules, pills, tablets, coated tablets and liquids or other known oral forms for dispensing can be used as pharmaceutical preparations. In this case, the pharmaceutical agents can be formulated in the way that they release the active ingredients either in a short time and pass on to the body or have a depot action, so that a longer-lasting, slow supply of active ingredients to the body is achieved. In addition to at least one benzimidazole derivative, the dosage units can contain one or more pharmaceutically compatible vehicles, for example substances for adjusting the rheology of the pharmaceutical agent, surfactants, solubilizers, microcapsules, microparticles, granulates, diluents, binders, such as starches, sugar, sorbitol and gelatins, also fillers, such as silicic acid and talc, lubricants, dyes, perfumes and other substances.

Corresponding tablets can be obtained by, for example, mixing an active ingredient with known adjuvants, for example inert diluents such as dextrose, sugar, sorbitol, mannitol, polyvinyl pyrrolidone, explosives such as corn starch or alginic acid, binders such as starch or gelatin, lubricants such as carboxypolymethylene, carboxy methyl cellulose, cellulose acetate phthalate or polyvinyl acetate. The tablets can also consist of several layers.

Coated tablets can be produced accordingly by coating cores that are produced analogously to the tablets with agents that are commonly used in tablet coatings, for example polyvinyl pyrrolidone or shellac, gum arabic, talc, titanium oxide or sugar. In this case, the shell of the coated tablet can also consist of several layers, whereby the adjuvants that are mentioned above in the case of the tablets can be used.

Capsules that contain active ingredients can be produced, for example, by the active ingredient being mixed with an inert vehicle such as lactose or sorbitol and encapsulated in gelatin capsules.

The benzimidazole derivatives according to the invention can also be formulated in the form of a solution that is intended for oral administration and that in addition to the active benzimidazole derivative contains as components a pharmaceutically compatible oil and/or a pharmaceutically compatible lipophilic surfactant and/or a pharmaceutically compatible hydrophilic surfactant and/or a pharmaceutically compatible water-miscible solvent.

To achieve better bio-availability of the active ingredients according to the invention, the compounds can also be formulated as cyclodextrin clathrates. To this end, the compounds are reacted with α-, β- or γ-cyclodextrin or derivatives thereof.

If creams, ointments, lotions and liquids that can be applied topically are to be used, the latter must be constituted so that the compounds according to the invention are fed to the body in adequate amounts. In these forms for dispensing, adjuvants are contained, for example substances for adjusting the rheology of pharmaceutical agents, surfactants, preservatives, solubilizers, diluents, substances for increasing the permeability of the benzimidazole derivatives according to the invention through the skin, dyes, perfumes and skin protection agents, such as conditioners and moisturizers. Together with the compounds according to the invention, other active ingredients can also be contained in the pharmaceutical agent [*Ullmanns Enzyklopädie der technischen Chemie [Ullmann's Encyclopedia of Technical Chemistry*], Volume 4 (1953), pages 1-39; *J. Pharm. Sci.*, 52, 918 ff. (1963); issued by Czetsch-Lindenwald, *Hiltsstoffe für Pharmazie und angrenzende Gebiete [Adjuvants for Pharmaceutics and Related Fields]; Pharm. Ind.*, 2, 72 ff (1961); Dr. H. P. Fiedler, *Lexikon der Hilfsstoffe für Pharmazie, Kosmetik und angrenzende Gebiete [Dictionary of Adjuvants for Pharmaceutics, Cosmetics and Related Fields*], Cantor AG, Aulendorf/Württ.; 1971].

The substances according to the invention can also be used in suitable solutions such as, for example, physiological common salt solution, as infusion or injection solutions. For parenteral administration, the active ingredients can be dissolved or suspended in a physiologically compatible diluent. As diluents, in particular oily solutions, such as, for example, solutions in sesame oil, castor oil and cottonseed oil, are suitable. To increase solubility, solubilizers, such as, for example, benzyl benzoate or benzyl alcohol, can be added.

To formulate an injectable preparation, any liquid vehicle can be used in which the compounds according to the invention are dissolved or emulsified. These liquids frequently also contain substances for regulating viscosity, surfactants, preservatives, solubilizers, diluents and other additives, with which the solution is set to isotonic. Other active ingredients can also be administered together with the benzimidazole derivatives.

It is also possible to incorporate the substances according to the invention in a transdermal system and thus to administer them transdermally. To this end, the benzimidazole derivatives are applied in the form of a depot injection or an implant preparation, for example subcutaneously. Such preparations can be formulated in such a way that a delayed release of active ingredients is made possible. To this end, known techniques can be used, for example depots that dissolve or operate with a membrane. Implants can contain as inert materials, for example, biodegradable polymers or synthetic silicones, for example silicone gum. The benzimidazole derivatives can also be incorporated in, for example, a patch, for percutaneous administration.

The dosage of the substances of general formula I according to the invention is determined by the attending physician and depends on, i.a., the substance that is administered, the method of administration, the disease that is to be treated and the severity of the disease. The daily dose is no more than 1000 mg, preferably no more than 100 mg, whereby the dose can be given as a single-dose to be administered once or divided into two or more daily doses.

The benzimidazoles of formula I are accessible in various ways according to processes that are known in the literature per se.

As possible processes in addition to others, the following can be mentioned:

1. By reaction of ortho-leaving group-substituted (preferably halogen-substituted) nitrobenzene derivatives (A) with arylamines (B), N-aryl-2-nitrobenzenes (C) can be produced under diverse reaction conditions, such as, for example, by heating reactants with or without a suitable inert solvent, such as, e.g., alkylbenzenes. Also, the amine that is used as a reactant can be used in excess as a solvent. The reactions are carried out both with and without bases (for example, potassium carbonate, sodium hydride). Other adjuvants, such as, e.g., copper salts, can also be used. Examples of the procedures that are indicated here are found in numerous works, such as, for example, in: D. Jerchel, H. Fischer, M. Graft, *Ann. Chem.*, 575, 162 (1952) *CAS*, 53 (2138); R.-A. Abramovitch, *Can J. Chem.*, 38, 2273, 1960).

SCHEMA 1

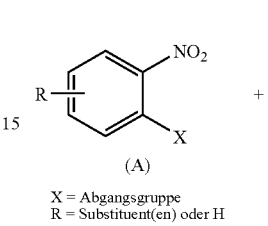

(A)

X = Abgangsgruppe
R = Substituent(en) oder H

(B)

(C)

[Key:]
SCHEMA 1 = DIAGRAM 1
Abgangsgruppe = Leaving group
Substituent (en) oder H = Subtituent(s) or H The thus obtained N-arylnitroaniline derivatives (C) can be converted in various ways into 1,2-disubstituted benzimidazoles (E):

SCHEMA 2

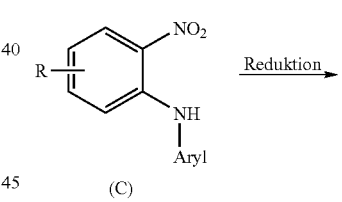

(C)

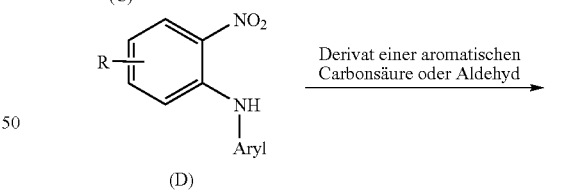

(D)

(E)

[Key:]
SCHEMA 2 = DIAGRAM 2
Reduktion = Reduction
Derivat einer aromatischen
Carbonsaüure oder Aldehyd = Derivative of an aromatic carboxylic acid or aldehyde The reduction of nitro group (C) is carried out preferably by hydrogenation in polar solvents such as acetic acid, lower alcohols or ethyl acetates with the addition of catalysts, such as Raney nickel or palladium on carbon, or by chemical reduction with, for example, tin in hydrochloric acid, $SnCl_2$ [F. D. Bellamy, *Tet. Lett.*, (1984)] or Fe/acetic acid [D. C. Owsily, J. J. Bloomfield, *Synthesis*, 118, 150 (1977)].

From the diamines (D), benzimidazoles (E) can be obtained by reaction with acid derivatives, such as orthoesters, iminoesters, acid anhydrides, aldehydes or else free carboxylic acids with or without acidic catalysis and/or dehydrating agents. As an example, here, the production of 1,2-diphenylbenzimidazole from benzoic acid and N-phenyl-o-phenylenediamine with use of triphenyl phosphine oxide and trifluoromethanesulfonic acid anhydride can be cited [J. B. Hendrickson, M. S. Hussoin, *J. Org. Chem.*, 52, 4137 (1987)].

When using aromatic aldehydes, for example, nitrobenzene is used as a solvent to be able to perform in situ the oxidation of the primary formed benzimidazoline. Also, the cyclization to benzimidazoles is accomplished by aromatic aldehydes being reacted as bisulfite adducts with diamines (D).

2. T. Benincori and F. Sannicolo in J. Heterocyclic Chem. 25, 1029 (1988) describe another access to benzimidazoles (E) that makes possible a broad variation of the substitution pattern both of the two aryl substituents and on the benzene ring of the benzimidazole. For one skilled in the art, it is obvious that these substituents must be compatible with the reactants and reaction conditions that are used in the course of the synthesis sequence. Sometimes, the substituents can be modified later. Here in the product, a hydroxy group is always contained in 6-position of the benzimidazole (cf. structure F).

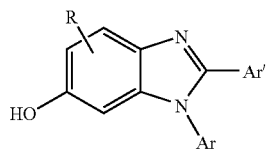

(F)

3. Finally, it can be mentioned that in some cases, the possibility exists of direct N-arylation of pre-fabricated benzimidazoles, e.g., according to M. J. Sansone; M. S. Kwiatck, U.S. Pat. No. 4,933,397, or D. M. T. Chan; K. L. Monaco; R.-P. Wang; M. P. Winters, Tet. Lett. 39 (1998) 2933 or A. P. Combs, S. Saubern, M. Rafalski, P. Y. S. Lam, Tet. Lett. 40 (1999) 1623.

It is obvious to one skilled in the art that substituents R must be compatible with the reagents and reaction conditions that are used in the course of the synthesis sequence. The substituents optionally can be modified later.

If structural element B—A—O (formula I) is established in protected or unprotected form because of incompatibility with the reaction conditions during the respective benzimidazole synthesis or for other synthetic reasons only after benzimidazole synthesis has been concluded, various procedures, depending on substituents $R^3$ that are entrained in the benzene ring of the benzimidazole, are possible for establishing the B—A—O structural element (formula I), whereby, as is obvious to one skilled in the art, a compatibility of the methods used with aryl substituents and other radicals $R^3$ must be considered.

Below are some possibilities for establishing the B—A—O structural element:

Oxygen can be entrained from the start in free form (e.g., R=OH in formula (A)) or else in protected form, for example as alkyl ether [cf., for example: B. D. Jerchel, H. Fischer, M. Graft, *Ann. Chem.*, 575, 162 (1952)] as a substituent in a benzimidazole synthesis. By alkyl ether cleavage, with, e.g., concentrated hydrobromic acid with the optional aid of solubilizers such as halogenated hydrocarbons or else with boron tribromide in inert solvents, such as, for example, dichloromethane, the hydroxyl group can be released. The hydroxyl group can be reacted according to known methods with optionally one terminal group B (Formula I) or alkyl halides that contain a precursor thereof to form the ethers, whereby the reaction is carried out with the alkylating agents preferably in polar solvents, such as, for example, dimethylformamide, dimethyl sulfoxide, ethers, such as, for example, tetrahydrofuran or else lower ketones, such as acetone or methylethyl ketone, with the addition of bases, such as alkali and alkaline-earth hydrides, but preferably sodium hydride, or with the addition of alkali carbonates, such as potassium or cesium carbonate, at a temperature range of 0° C. to 120° C. In addition, a reaction can be carried out in a two-phase system with phase transfer catalysis, whereby the reactants are dissolved in a suitable inert organic solvent, such as, for example, in haloalkanes, but preferably in dichloromethane. The other phase is a solid alkali hydroxide, preferably sodium or potassium hydroxide, or else a concentrated aqueous solution of the hydroxide in question. As phase transfer catalysts, for example, quaternary ammonium salts are used. Reactions under phase transfer catalysis are preferably carried out at room temperature.

For example, a compound of formula A (with R=OH) is dissolved in dimethylformamide and reacted with the addition of cesium carbonate with 6-bromohexanoic acid methyl ester at temperatures of 0° C. to 50° C. The cleavage of the ester by acidic or alkaline hydrolysis can be carried out according to methods that are known to one skilled in the art, such as, for example, with basic catalysts, such as, for example, with alkali or alkaline-earth carbonates or -hydroxides in water or the aqueous solution of an alcohol. As alcohols, aliphatic alcohols, such as, for example, methanol, ethanol, butanol, etc., are considered, but preferably methanol. Aqueous solutions of ethers, such as tetrahydrofuran, are also used. As alkali carbonates and alkali hydroxides, lithium, sodium and potassium salts can be mentioned. Preferred are the lithium and sodium salts. As alkaline-earth carbonates and hydroxides, for example, calcium carbonate, calcium hydroxide and barium carbonate are suitable. The reaction is generally carried out at −10° C. to 70° C., but preferably at 25° C. The ester cleavage can also be carried out, however, under acidic conditions, such as, for example, in aqueous hydrochloric acid, optionally with the aid of a solubilizer, such as, for example, a lower alcohol, preferably methanol.

From a nitrile that is present in the alkylating reagent or else generated later, a carboxylic acid group can be generated by hydrolysis. The alkylating reagents can also contain functional groups such as, for example, hydroxyl groups in free or protected form, which can be exchanged after conversion into leaving groups, such as, for example, tosylate, mesylate, bromide or iodide, for example, for amino or alkyl groups. Also, the alkylating reagents can contain functional groups, such as, for example, halogens or optionally protected amino groups, which can then be further modified.

Depending on the substitution desired, substituents $R^3$ are contained in the synthesis components from the start or are established if necessary at suitable sites of the synthesis sequence in question or are generated from suitable precursors that are entrained.

The free acid derivatives of Formula I or ester precursors can be converted according to diverse processes that are known in the literature into amide derivatives of Formula I.

The free acid derivatives of Formula I can also be converted with neutralization to salts with suitable amounts of the corresponding inorganic bases. For example, when the corresponding acids are dissolved in water, which contains stoichiometric amounts of the base, the solid salt is obtained after the water is evaporated or after a water-miscible solvent, for example alcohol or acetone, is added.

The amine salts can be produced in the usual way. To this end, the corresponding acid is dissolved in a suitable solvent, such as, for example, ethanol, acetone, diethyl ether or benzene, and one to five equivalents of the respective amine is added to this solution. In this case, the salt usually accumulates in solid form or is isolated after the solvent is evaporated in the usual way.

The clathrates with α-, β-, or γ-cyclodextrin are obtained analogously to the instructions in WO-A-87/05294. β-Cyclodextrin is preferably used. Liposomes are produced according to the process that is described in *Pharmazie in unserer Zeit [Pharmaceutics in Our Time]*, 11, 98 (1982).

Below, the production of several precursors, intermediate products and products is described by way of example. If the production of the starting compounds is not described, the starting compounds are known and commercially available, or the compounds are synthesized analogously to the described processes.

In the production of the substances according to the invention, for example, the following processes are used:

General Operating Instructions 1:

Reduction of Nitro Groups

The compound that is to be reduced is dissolved in ethyl acetate, tetrahydrofuran, methanol or ethanol or mixtures of the solvent, and it is hydrogenated to 2 to 5% (relative to the nitro compound) palladium on carbon (10%) at normal pressure. After hydrogen absorption has ended, it is suctioned off, the residue is washed with ethyl acetate or methanol or ethanol, and the filtrate is concentrated by evaporation in a vacuum. The crude product is reacted generally without further purification.

General Operating Instructions 2:

Ether Cleavage with Hydrobromic Acid 5 g of arylmethyl ether is mixed with 160 ml of 48% aqueous HBr and refluxed for 1-5 hours. After cooling, it is filtered. The residue is taken up in ethyl acetate and extracted three times with saturated sodium bicarbonate solution. After drying on sodium sulfate, it is concentrated by evaporation in a vacuum. If necessary, the residue is purified on silica gel by crystallization or column chromatography.

General Operating Instructions 3:

Alkylation of Hydroxybenzimidazole Derivatives and Phenol Derivatives with Alkyl Halides A solution of 1.85 mmol of the hydroxybenzimidazole derivative in 12 ml of N,N-dimethylformamide is mixed with 1.85 mmol of cesium carbonate and 2.24 mmol of alkyl bromide or alkyl iodide. When alkyl bromides are used, 1.85 mmol of sodium iodide is optionally added. It is stirred for 12 to 96 hours, then poured onto water, taken up with ethyl acetate, the organic phase is washed four times with water, dried on sodium sulfate and concentrated by evaporation in a vacuum.

As an alternative to this aqueous working-up, the reaction mixture can be mixed with dichloromethane, separated from the precipitating salts by filtration and the filtrate concentrated by evaporation in a vacuum.

Independently of the working-up method, the residue is purified by crystallization or column chromatography on silica gel.

General Operating Instructions 4:

Saponification of Carboxylic Acid Alkyl Esters 0.77 mmol of the carboxylic acid alkyl ester is dissolved in 5 ml of methanol and 5 ml of tetrahydrofuran, and it is mixed with 5 ml of a 0.5N aqueous lithium or sodium hydroxide solution. After 2 to 12 hours of stirring, it is concentrated by evaporation in a vacuum to a very large extent, neutralized by the addition of aqueous hydrochloric acid and extracted with ethyl acetate. It is dried on sodium sulfate and concentrated by evaporation in a vacuum. The residue is purified, if necessary, by column chromatography on silica gel.

General Operating Instructions 5:

Cyclization to Benzimidazoles with Aldehydes 1 mmol of a 1,2-diaminobenzene derivative is dissolved in 3 ml of nitrobenzene. 1 mmol of an aryl aldehyde or heteroaryl aldehyde is added to this. It is heated for 2-6 hours to 150° C. and allowed to cool. The residue is purified directly by column chromatography on silica gel without additional working-up.

General Operating Instructions 6:

Conversion of Carboxylic Acid Esters to Carboxylic Acid Amides 0.36 mmol of an amine is dissolved in 3 ml of toluene and mixed drop by drop with 0.18 ml of a 2 M solution of trimethylaluminum in toluene while being cooled in an ice bath. It is mixed with a solution that consists of 0.33 mmol of carboxylic acid methyl ester in 3 ml of toluene, and it is stirred for 2 to 8 hours at 95° C. For working-up, water is added after cooling, it is extracted three times with ethyl acetate, the combined organic phases are washed with saturated sodium chloride solution, dried on sodium sulfate and concentrated by evaporation in a vacuum. The residue is purified by column chromatography on silica gel.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

EXAMPLE 1

6-[[1-(4-Methylphenyl)-2-(3-pyridinyl)-1H-benzimidazol-6-yl]oxy]hexanoic acid a) 3-(4-Methylphenyl)amino-4-nitrophenol 5.4 g of 3-fluoro-4-nitrophenol and 4.8 ml of 4-methylaniline were mixed and stirred for 6 hours at 120° C. After cooling, it was taken up in ethyl acetate and water and extracted three times with 1N aqueous hydrochloric acid. The combined aqueous phases were extracted three times with ethyl acetate. The combined organic phases were dried on sodium sulfate, concentrated by evaporation in a vacuum, and the residue was crystallized.

MS (EI): 244 (molecular ion peak)

b) 6-[3-(4-Methylphenyl)amino-4-nitrophenyl]oxy-hexanoic acid methyl ester was obtained by reaction of 3-(4-methylphenyl)amino-4-nitrophenol with 6-bromohexanoic acid methyl ester according to general operating instructions 3.

MS (EI): 372 (molecular ion peak)

c) 6-[[4-Amino-3-((4-methylphenyl)amino)phenyl]oxy]hexanoic acid methyl ester was obtained by reaction of 6-[3-(4-methylphenyl)amino-4-nitrophenyl]oxy-hexanoic acid methyl ester according to general operating instructions 1.

MS (EI): 342 (molecular ion peak)

d) 6-[[1-(4-Methylphenyl)-2-(3-pyridinyl)-1H-benzimidazol-6-yl]oxy]hexanoic acid methyl ester was obtained by reaction of 6-[[4-amino-3-((4-methylphenyl)amino)-phenyl]oxy]hexanoic acid methyl ester with 3-pyridylcarbaldehyde according to general operating instructions 5.

MS (EI): 429 (molecular ion peak)

e) 6-[[1-(4-Methylphenyl)-2-(3-pyridinyl)-1H-benzimidazol-6-yl]oxy]hexanoic acid was produced by reaction of 6-[[1-(4-methylphenyl)-2-(3-pyridinyl)-1H-benzimidazol-6-yl]oxy]hexanoic acid methyl ester according to general operating instructions 4.

MS (EI): 415 (molecular ion peak)

EXAMPLE 2

5-[[1-(4-Methylphenyl)-2-(3-pyridinyl)-1H-benzimidazol-6-yl]oxy]pentanoic acid a) 5-[3-(4-Methylphenyl)amino-4-nitrophenyl]oxy-pentanoic acid methyl ester was obtained by reaction of 3-(4-methylphenyl)amino-4-nitrophenol with 5-bromopentanoic acid methyl ester according to general operating instructions 3.

MS (EI): 358 (molecular ion peak)

b) 5-[[4-Amino-3-((4-methylphenyl)amino)phenyl]oxy]pentanoic acid methyl ester was obtained by reaction of 5-[3-(4-methylphenyl)amino-4-nitrophenyl]-oxypentanoic acid methyl ester according to general operating instructions 1.

MS (EI): 328 (molecular ion peak)

c) 5-[[1-(4-Methylphenyl)-2-(3-pyridinyl)-1H-benzimidazol-6-yl]oxy]pentanoic acid methyl ester was obtained by reaction of 5-[[4-amino-3-((4-methylphenyl)amino)-phenyl]oxy]pentanoic acid methyl ester with 3-pyridylcarbaldehyde according to general operating instructions 5.

MS (EI): 415 (molecular ion peak)

d) 5-[[1-(4-Methylphenyl)-2-(3-pyridinyl)-1H-benzimidazol-6-yl]oxy]pentanoic acid was produced by reaction of 5-[[1-(4-methylphenyl)-2-(3-pyridinyl)-1H-benzimidazol-6-yl]oxy]pentanoic acid methyl ester according to general operating instructions 4.

MS (EI): 401 (molecular ion peak)

EXAMPLE 3

4-[[1-(4-Methylphenyl)-2-(3-pyridinyl)-1H-benzimidazol-6-yl]oxy]butyric acid a) 4-[3-(4-Methylphenyl)amino-4-nitrophenyl]oxy-butyric acid methyl ester was obtained by reaction of 3-(4-methylphenyl)amino-4-nitrophenol with 4-bromobutyric acid methyl ester according to general operating instructions 3.

MS (EI): 344 (molecular ion peak)

b) 4-[[4-Amino-3-((4-methylphenyl)amino)phenyl]oxy]butyric acid methyl ester was obtained by reaction of 4-[3-(4-methylphenyl)amino-4-nitrophenyl]-oxybutyric acid methyl ester according to general operating instructions 1.

MS (EI): 314 (molecular ion peak)

c) 4-[[1-(4-Methylphenyl)-2-(3-pyridinyl)-1H-benzimidazol-6-yl]oxy]butyric acid methyl ester was obtained by reaction of 4-[[4-amino-3-((4-methylphenyl)amino)-phenyl]oxy]butyric acid methyl ester with 3-pyridyl carbaldehyde according to general operating instructions 5.

MS (EI): 401 (molecular ion peak)

d) 4-[[1-(4-Methylphenyl)-2-(3-pyridinyl)-1H-benzimidazol-6-yl]oxy]butyric acid was produced by reaction of 4-[[1-(4-methylphenyl)-2-(3-pyridinyl)-1H-benzimidazol-6-yl]oxy]butyric acid methyl ester according to general operating instructions 4.

MS (EI): 387 (molecular ion peak)

EXAMPLE 4

6-[[1-(4-Methylphenyl)-2-(4-pyridinyl)-1H-benzimidazol-6-yl]oxy]hexanoic acid a) 6-[[1-(4-Methylphenyl)-2-(4-pyridinyl)-1H-benzimidazol-6-yl]oxy]hexanoic acid methyl ester was obtained by reaction of 6-[[4-amino-3-((4-methylphenyl)amino)-phenyl]oxy]hexanoic acid methyl ester with 4-pyridyl carbaldehyde according to general operating instructions 5.

MS (EI): 429 (molecular ion peak)

b) 6-[[1-(4-Methylphenyl)-2-(4-pyridinyl)-1H-benzimidazol-6-yl]oxy]hexanoic acid was produced by reaction of 6-[[1-(4-methylphenyl)-2-(4-pyridinyl)-1H-benzimidazol-6-yl]oxy]hexanoic acid methyl ester according to general operating instructions 4.

MS (EI): 415 (molecular ion peak)

EXAMPLE 5

6-[[1-(4-Methylphenyl)-2-(3-thienyl)-1H-benzimidazol-6-yl]oxy]hexanoic acid a) 6-[[1-(4-Methylphenyl)-2-(3-thienyl)-1H-benzimidazol-6-yl]oxy]hexanoic acid methyl ester was obtained by reaction of 6-[[4-amino-3-((4-methylphenyl)amino)-phenyl]oxy]hexanoic acid methyl ester with 3-thienyl carbaldehyde according to general operating instructions 5.

MS (EI): 434 (molecular ion peak)

b) 6-[[1-(4-Methylphenyl)-2-(3-thienyl)-1H-benzimidazol-6-yl]oxy]hexanoic acid was produced by reaction of 6-[[1-(4-methylphenyl)-2-(3-thienyl)-1H-benzimidazol-6-yl]oxy]hexanoic acid methyl ester according to general operating instructions 4.

MS (EI): 420 (molecular ion peak)

EXAMPLE 6

5-[[1-(4-Methylphenyl)-2-(3-thienyl)-1H-benzimidazol-6-yl]oxy]pentanoic acid a) 5-[[1-(4-Methylphenyl)-2-(3-thienyl)-1H-benzimidazol-6-yl]oxy]pentanoic acid methyl ester was obtained by reaction of 5-[[4-amino-3-((4-methylphenyl)-amino)phenyl]oxy]pentanoic acid methyl ester with 3-thienyl-carbaldehyde according to general operating instructions 5.

MS (EI): 420 (molecular ion peak)

b) 5-[[1-(4-Methylphenyl)-2-(3-thienyl)-1H-benzimidazol-6-yl]oxy]pentanoic acid was produced by reaction of 5-[[1-(4-methylphenyl)-2-(3-thienyl)-1H-benzimidazol-6-yl]oxy]pentanoic acid methyl ester according to general operating instructions 4.

MS (EI): 406 (molecular ion peak)

EXAMPLE 7

4-[[1-(4-Methylphenyl)-2-(3-thienyl)-1H-benzimidazol-6-yl]oxy]butyric acid a) 4-[[1-(4-Methylphenyl)-2-(3-thienyl)-1H-benzimidazol-6-yl]oxy]butyric acid methyl ester was obtained by reaction of 4-[[4-amino-3-((4-methylphenyl)-amino)phenyl]oxy]butyric acid methyl ester with 3-thiophene carbaldehyde according to general operating instructions 5.

MS (EI): 406 (molecular ion peak)

b) 4-[[1-(4-Methylphenyl)-2-(3-thienyl)-1H-benzimidazol-6-yl]oxy]butyric acid was produced by reaction of 4-[[1-(4-methylphenyl)-2-(3-thienyl)-1H-benzimidazol-6-yl]oxy]butyric acid methyl ester according to general operating instructions 4.

MS (EI): 392 (molecular ion peak)

EXAMPLE 8

5-[[1-Phenyl-2-(3-thienyl)-1H-benzimidazol-6-yl]oxy]pentanoic acid a) 4-Methoxy-$N^2$-phenyl-o-phenylenediamine was obtained by reaction of (5-methoxy-2-nitrophenyl)phenylamine [Kottenhahn et al.; J. Org. Chem.; 28; 1963; 3114, 3118; Banthorpe; Cooper; J. Chem. Soc. B; 1968; 605] according to general operating instructions 1.

$^1$H-NMR (CDCl$_3$): δ=3.42 ppm s (broad) (2H); 3.72 s (3H); 5.33 s (broad)(1H); 6.56 dd (J=10, 2 Hz, 1H); 6.76 d (J=10 Hz, 1H); 6.79 d (J=2 Hz, 1H); 6.82-6.90 m (3H); 7.25 dd (J=8, 8 Hz, 2H).

b) 6-Methoxy-1-phenyl-2-(3-thienyl)-1H-benzimidazole was obtained by reaction of 4-methoxy-$N^2$-phenyl-o-phenylenediamine with thiophene-3-carbaldehyde according to general operating instructions 5.

MS (EI): 306 (molecular ion peak)

c) 6-Hydroxy-1-phenyl-2-(3-thienyl)-1H-benzimidazole was obtained by reaction of 6-methoxy-1-phenyl-2-(3-thienyl)-1H-benzimidazole according to general operating instructions 2.

MS (EI): 292 (molecular ion peak)

d) 5-[[1-Phenyl-2-(3-thienyl)-1H-benzimidazol-6-yl]oxy]pentanoic acid methyl ester was obtained by reaction of 6-hydroxy-1-phenyl-2-(3-thienyl)-1H-benzimidazole with 5-bromopentanoic acid methyl ester according to general operating instructions 3.

MS (EI): 406 (molecular ion peak)

e) 5-[[1-Phenyl-2-(3-thienyl)-1H-benzimidazol-6-yl]oxy]pentanoic acid was obtained by reaction of 5-[[1-phenyl-2-(3-thienyl)-1H-benzimidazol-6-yl]oxy]pentanoic acid methyl ester according to general operating instructions 4.

MS (EI): 392 (molecular ion peak)

EXAMPLE 9

4-[[1-Phenyl-2-(3-thienyl)-1H-benzimidazol-6-yl]oxy]butyric acid a) 4-[[1-Phenyl-2-(3-thienyl)-1H-benzimidazol-6-yl]oxy]butyric acid methyl ester was obtained by reaction of 6-hydroxy-1-phenyl-2-(3-thienyl)-1H-benzimidazole with 4-bromobutanoic acid methyl ester according to general operating instructions 3.

MS (EI): 392 (molecular ion peak)

b) 4-[[1-Phenyl-2-(3-thienyl)-1H-benzimidazol-6-yl]oxy]butyric acid was obtained by reaction of 4-[[1-phenyl-2-(3-thienyl)-1H-benzimidazol-6-yl]oxy]butyric acid methyl ester according to general operating instructions 4.

MS (EI): 378 (molecular ion peak)

EXAMPLE 10

6-[[1-Phenyl-2-(3-thienyl)-1H-benzimidazol-6-yl]oxy]hexanoic acid a) 6-[[1-Phenyl-2-(3-thienyl)-1H-benzimidazol-6-yl]oxy]hexanoic acid methyl ester was obtained by reaction of 6-hydroxy-1-phenyl-2-(3-thienyl)-1H-benzimidazole with 6-bromohexanoic acid methyl ester according to general operating instructions 3.

MS (EI): 420 (molecular ion peak)

b) 6-[[1-Phenyl-2-(3-thienyl)-1H-benzimidazol-6-yl]oxy]hexanoic acid was obtained by reaction of 6-[[1-phenyl-2-(3-thienyl)-1H-benzimidazol-6-yl]oxy]hexanoic acid methyl ester according to general operating instructions 4.

MS (EI): 406 (molecular ion peak)

EXAMPLE 11

6-[[1-(4-Fluorophenyl)-2-(3-thienyl)-1H-benzimidazol-6-yl]oxy]hexanoic acid a) (5-Chloro-2-nitrophenyl)-(4-fluorophenyl)amine 50 g of 1-chloro-3,4-dinitrobenzene in 250 ml of ethanol is mixed with 50 ml of 4-fluoroaniline and stirred for 35 hours at 60° C. After concentration by evaporation to half the volume, water and dichloromethane are divided up. After the organic phase is washed with 1N aqueous hydrochloric acid, it is dried on sodium sulfate, filtered and concentrated by evaporation. After chromatography on silica gel, 62.33 g of (5-chloro-2-nitrophenyl)-(4-fluorophenyl)amine is obtained.

$^1$H-NMR (CDCl$_3$): δ=6.71 dd (J=9, 2 Hz, 1H); 6.97 d (J=2 Hz, 1H); 7.13 dd (J=9, 9 Hz, 2H); 7.22 dd (J=9, 6 Hz, 2H); 8.15 d (J=10 Hz, 1H); 9.45 s (br)(1H).

b) (5-Methoxy-2-nitrophenyl)-(4-fluorophenyl)amine 36.44 g (5-chloro-2-nitrophenyl)-(4-fluorophenyl)amine was added to a solution that consists of 6.6 g of sodium in 450 ml of methanol, and it was refluxed for 16 hours. After another 30 hours of stirring at 60° C., it was cooled, and the crystalline product was suctioned off. 34 g of (5-methoxy-2-nitrophenyl)-(4-fluorophenyl)amine was obtained.

$^1$H-NMR (CDCl$_3$): δ=3.72 s (3H); 6.44 dd (J=9, 2 Hz, 1H); 6.48 d (J=2 Hz, 1H); 7.13 dd (J=9, 9 Hz, 2H); 7.27 dd (9, 6 Hz, 2H); 8.20 d (J=9 Hz, 1H); 9.65 s (br)(1H).

c) N$^2$-(4-Fluorophenyl)-4-methoxybenzene-1,2-diamine 33.5 g (0.128 ml) of (5-methoxy-2-nitrophenyl)-(4-fluorophenyl)amine was reacted according to general operating instructions 1. The crude product was further processed without purification.

$^1$H-NMR (CDCl$_3$): δ=3.70 ppm s (3H); 6.49 d(br) (J=9 Hz, 1H); 6.68 d (J=2 Hz, 1H); 6.78-6.97 m (5H).

d) 6-Methoxy-1-(4-fluorophenyl)-2-(3-thienyl)-1H-benzimidazole 7.48 g of thiophene-3-aldehyde was stirred in 65 ml of 40% NaHSO$_3$ solution for two hours. After 15 g of N$^2$-(4-fluorophenyl)-4-methoxybenzene-1,2-diamine in 50 ml of ethanol was added, it was boiled for 4 hours, and stirring was continued overnight. The batch was dispersed between water and ethyl acetate, and the organic phase was washed with water. After drying on sodium sulfate and concentration by evaporation of the filtrate, 18.1 g of crude 6-methoxy-1-(4-fluorophenyl)-2-(3-thienyl)-1H-benzimidazole is obtained.

Flash point 154-158° C.

e) 6-Hydroxy-1-(4-fluorophenyl)-2-(3-thienyl)-1H-benzimidazole 18 g (55.5 mmol) of 6-methoxy-1-(4-fluorophenyl)-2-(3-thienyl)-1H-benzimidazole is reacted analogously to general operating instructions 2. 12.65 g (40 mmol) of crude 6-hydroxy-1-(4-fluorophenyl)-2-(3-thienyl)-1H-benzimidazole was obtained.

Flash point 212-218° C.

f) 6-[[1-(4-Fluorophenyl)-2-(3-thienyl)-1H-benzimidazol-6-yl]oxy]hexanoic acid methyl ester 6-Hydroxy-1-(4-fluorophenyl)-2-(3-thienyl)-1H-benzimidazole was reacted with 6-bromo-hexanoic acid methyl ester according to general operating instructions 3.

Flash point 131-134° C.

g) 6-[[1-(4-Fluorophenyl)-2-(3-thienyl-1H-benzimidazol-6-yl]oxy]hexanoic acid was obtained by reaction of 6-[[1-(4-fluorophenyl)-2-(3-thienyl)-1H-benzimidazol-6-yl]oxy]hexanoic acid methyl ester according to general operating instructions 4.

Flash point 170-175° C.

EXAMPLE 12

5-[[1-(4-Fluorophenyl)-2-(3-thienyl)-1H-benzimidazol-6-yl]oxy]pentanoic acid a) 5-[[1-(4-Fluorophenyl-2-(3-thienyl)-1H-benzimidazol-6-yl]oxy]pentanoic acid methyl ester 6-Hydroxy-1-(4-fluorophenyl)-2-(3-thienyl)-1H-benzimidazole was reacted according to general operating instructions 3 with 5-bromopentanoic acid methyl ester.

Flash point 90.5-92.5° C.

b) 5-[[1-(4-Fluorophenyl)-2-(3-thienyl)-1H-benzimidazol-6-yl]oxy]pentanoic acid

5-[[1-(4-Fluorophenyl-2-(3-thienyl)-1H-benzimidazol-6-yl]oxy]pentanoic acid methyl ester was reacted according to general instructions 4.

Flash point 184-189° C.

EXAMPLE 13

6-[[1-(4-Fluorophenyl)-2-(3-pyridinyl)-1H-benzimidazol-6-yl]oxy]hexanoic acid a) 6-Methoxy-1-(4-fluorophenyl)-2-(3-pyridinyl)-1H-benzimidazole $N^2$-(4-Fluorophenyl)-4-methoxybenzene-1,2-diamine was reacted analogously to Example 11d with pyridine-3-carbaldehyde.
Flash point 132.5-134° C.

b) 6-Hydroxy-1-(4-fluorophenyl)-2-(3-pyridinyl)-1H-benzimidazole

6-Methoxy-1-(4-fluorophenyl)-2-(3-pyridinyl)-1H-benzimidazole was reacted according to general operating instructions 2.
Flash point 238-241° C.

c) 6-[[1-(4-Fluorophenyl)-2-(3-pyridinyl)-1H-benzimidazol-6-yl]oxy]hexanoic acid methyl ester 6-Hydroxy-1-(4-fluorophenyl)-2-(3-pyridinyl)-1H-benzimidazole was reacted with 6-bromohexanoic acid methyl ester according to general operating instructions 3.
Flash point 105.5-111.5° C.

d) 6-[[1-(4-Fluorophenyl)-2-(3-pyridinyl)-1H-benzimidazol-6-yl]oxy]hexanoic acid was obtained by reaction of 6-[[1-(4-fluorophenyl)-2-(3-pyridinyl)-1H-benzimidazol-6-yl]oxy]hexanoic acid methyl ester according to general operating instructions 4.
Flash point 127.5-129° C.

EXAMPLE 14

5-[[1-(4-Fluorophenyl)-2-(3-pyridinyl)-1H-benzimidazol-6-yl]oxy]pentanoic acid a) 5-[[1-(4-Fluorophenyl)-2-(3-pyridinyl)-1H-benzimidazol-6-yl]oxy]pentanoic acid methyl ester 6-Hydroxy-1-(4-fluorophenyl)-2-(3-pyridinyl)-1H-benzimidazole was reacted with 5-bromo-pentanoic acid methyl ester according to general operating instructions 3.
Flash point 52-55° C.

b) 5-[[1-(4-Fluorophenyl)-2-(3-pyridinyl)-1H-benzimidazol-6-yl]oxy]pentanoic acid was obtained by reaction of 5-[[1-(4-fluorophenyl)-2-(3-pyridinyl)-1H-benzimidazol-6-yl]oxy]pentanoic acid methyl ester according to general operating instructions 4.
Flash point 181.5-183° C.

EXAMPLE 15

5-[[1-Phenyl-2-(3-pyridinyl)-1H-benzimidazol-6-yl]oxy]pentanoic acid a) 6-Methoxy-1-phenyl-2-(3-pyridinyl)-1H-benzimidazole was obtained by reaction of 4-methoxy-$N^2$-phenyl-o-phenylenediamine with pyridine-3-carbaldehyde according to general operating instructions 5.
MS (EI): 301 (molecular ion peak)

b) 6-Hydroxy-1-phenyl-2-(3-pyridinyl)-1H-benzimidazole was obtained by reaction of 6-methoxy-1-phenyl-2-(3-pyridinyl)-1H-benzimidazole according to general operating instructions 2.
$^1$H-NMR (D$_6$-DMSO): δ=6.52 ppm d (J=2 Hz, 1H); 6.81 dd (J=8, 2 Hz, 1H); 7.34-7.48 m (3H); 7.53-7.68 m (4H); 7.80 (ddd, J=8, 2, 1 Hz, 1H); 8.53 dd (J=2, 1 Hz, 1H); 8.67 d (J=1 Hz, 1H); 9.42 (s, 1H).

c) 5-[[1-Phenyl-2-(3-pyridinyl)-1H-benzimidazol-6-yl]oxy]pentanoic acid methyl ester was obtained by reaction of 6-hydroxy-1-phenyl-2-(3-pyridinyl)-1H-benzimidazole with 5-bromopentanoic acid methyl ester according to general operating instructions 3.
MS (EI): 401 (molecular ion peak)

d) 5-[[1-Phenyl-2-(3-pyridinyl)-1H-benzimidazol-6-yl]oxy]pentanoic acid was obtained by reaction of 5-[[1-phenyl-2-(3-pyridinyl)-1H-benzimidazol-6-yl]oxy]pentanoic acid methyl ester according to general operating instructions 4.
$^1$H-NMR (CD$_3$OD): δ=1.72-1.88 m (4H); 2.30 t (J=8 Hz, 2H); 3.98 t (J=8 Hz, 2H); 6.72 ppm d (J=2 Hz, 1H); 7.03 dd (J=8, 2 Hz, 1H); 7.40-7.48 m (3H); 7.55-7.65 m (3H); 7.70 (d, J=8 Hz, 1H); 7.92 ddd (J=8, 2, 1 Hz, 1H); 8.53 dd (J=8, 2 Hz, 1H); 8.70 dd (J=2, 1 Hz, 1H).

EXAMPLE 16

4-[[1-Phenyl-2-(3-pyridinyl)-1H-benzimidazol-6-yl]oxy]butyric acid a) 4-[[1-Phenyl-2-(3-pyridinyl)-1H-benzimidazol-6-yl]oxy]butyric acid methyl ester was obtained by reaction of 6-hydroxy-1-phenyl-2-(3-pyridinyl)-1H-benzimidazole with 4-bromobutanoic acid methyl ester according to general operating instructions 3.
MS (EI): 387 (molecular ion peak)

b) 4-[[1-Phenyl-2-(3-pyridinyl)-1H-benzimidazol-6-yl]oxy]butyric acid was obtained by reaction of 4-[[1-phenyl-2-(3-pyridinyl)-1H-benzimidazol-6-yl]oxy]butyric acid methyl ester according to general operating instructions 4.
MS (EI): 373 (molecular ion peak)

EXAMPLE 17

6-[[1-Phenyl-2-(3-pyridinyl)-1H-benzimidazol-6-yl]oxy]hexanoic acid a) 6-[[1-Phenyl-2-(3-pyridinyl)-1H-benzimidazol-6-yl]oxy]hexanoic acid methyl ester was obtained by reaction of 6-hydroxy-1-phenyl-2-(3-pyridinyl)-1H-benzimidazole with 6-bromohexanoic acid methyl ester according to general operating instructions 3.
MS (EI): 415 (molecular ion peak)

b) 6-[[1-Phenyl-2-(3-pyridinyl)-1H-benzimidazol-6-yl]oxy]hexanoic acid was obtained by reaction of 6-[[1-phenyl-2-(3-pyridinyl)-1H-benzimidazol-6-yl]oxy]hexanoic acid methyl ester according to general operating instructions 4.

MS (EI): 401 (molecular ion peak)

EXAMPLE 18

N-(3-Methoxypropyl)-6-[[1-(4-methylphenyl)-2-(3-pyridinyl)-1H-benzimidazol-6-yl]oxy]hexanamide was produced by reaction of 6-[[1-(4-methylphenyl)-2-(3-pyridinyl)-1H-benzimidazol-6-yl]oxy]hexanoic acid methyl ester with 3-methoxypropylamine according to general operating instructions 6.

MS (EI): 486 (molecular ion peak)

EXAMPLE 19

6-[[1-(4-Methylphenyl)-2-(3-pyridinyl)-1H-benzimidazol-6-yl]oxyl]-1-morpholin-1-ylhexan-1-one was produced by reaction of 6-[[1-(4-methylphenyl)-2-(3-pyridinyl)-1H-benzimidazol-6-yl]oxy]hexanoic acid methyl ester with morpholine according to general operating instructions 6.

MS (EI): 442 (molecular ion peak)

EXAMPLE 20

N-Methyl-6-[[1-(4-methylphenyl)-2-(3-pyridinyl)-1H-benzimidazol-6-yl]oxy]hexanamide was produced by reaction of 6-[[1-(4-methylphenyl)-2-(3-pyridinyl)-1H-benzimidazol-6-yl]oxy]hexanoic acid methyl ester with N-methylamine hydrochloride according to general operating instructions 6.

MS (EI): 428 (molecular ion peak)

EXAMPLE 21

N,N-Dimethyl-6-[[1-(4-methylphenyl)-2-(3-pyridinyl)-1H-benzimidazol-6-yl]oxy]hexanamide was produced by reaction of 6-[[1-(4-methylphenyl)-2-(3-pyridinyl)-1H-benzimidazol-6-yl]oxy]hexanoic acid methyl ester with dimethylamine hydrochloride according to general operating instructions 6.

MS (EI): 442 (molecular ion peak)

EXAMPLE 22

6-[[1-(4-Methylphenyl)-2-(3-pyridinyl)-1H-benzimidazol-6-yl]oxy]hexanamide was produced by reaction of 6-[[1-(4-methylphenyl)-2-(3-pyridinyl)-1H-benzimidazol-6-yl]oxy]hexanoic acid methyl ester with ammonium chloride according to general operating instructions 6.

MS (EI): 414 (molecular ion peak)

EXAMPLE 23

N-Cyclopropyl-6-[[1-(4-methylphenyl)-2-(3-thienyl)-1H-benzimidazol-6-yl]oxy]hexanamide was produced by reaction of 6-[[1-(4-methylphenyl)-2-(3-thienyl)-1H-benzimidazol-6-yl]oxy]hexanoic acid methyl ester with cyclopropylamine according to general operating instructions 6.

MS (EI): 459 (molecular ion peak)

EXAMPLE 24

N-Methyl-6-[[1-(4-methylphenyl)-2-(-3-thienyl)-1H-benzimidazol-6-yl]oxy]hexanamide was produced by reaction of 6-[[1-(4-methylphenyl)-2-(3-thienyl)-1H-benzimidazol-6-yl]oxy]hexanoic acid methyl ester with N-methylamine hydrochloride according to general operating instructions 6.

MS (EI): 433 (molecular ion peak)

EXAMPLE 25

N-(2-Methoxyethyl)-5-[[1-(4-methylphenyl)-2-(3-pyridinyl)-1H-benzimidazol-6-yl]oxy]pentanamide was produced by reaction of 5-[[1-(4-methylphenyl)-2-(3-pyridinyl)-1H-benzimidazol-6-yl]oxy]pentanoic acid methyl ester with 2-methoxyethylamine according to general operating instructions 6.

MS (EI): 458 (molecular ion peak)

EXAMPLE 26

N,N-Dimethyl-5-[[1-(4-methylphenyl)-2-(3-pyridinyl)-1H-benzimidazol-6-yl]oxy]pentanamide was produced by reaction of 5-[[1-(4-methylphenyl)-2-(3-pyridinyl)-1H-benzimidazol-6-yl]oxy]pentanoic acid methyl ester (Example 56c) with dimethylamine according to general operating instructions 6.

MS (EI): 428 (molecular ion peak)

EXAMPLE 27

5-[[1-(4-Methylphenyl)-2-(3-pyridinyl)-1H-benzimidazol-6-yl]oxy]pentanamide was produced by reaction of 5-[[1-(4-methylphenyl)-2-(3-pyridinyl)-1H-benzimidazol-6-yl]oxy]pentanoic acid methyl ester with ammonium chloride according to general operating instructions 6.

MS (EI): 400 (molecular ion peak)

EXAMPLE 28

6-[[1-(4-Methylphenyl)-2-(2-thienyl)-1H-benzimidazol-6-yl]oxy]hexanoic acid a) 6-[[1-(4-Methylphenyl)-2-(2-thienyl)-1H-benzimidazol-6-yl]oxy]hexanoic acid methyl ester was obtained by reaction of 6-[[4-amino-3-((4-methylphenyl)amino)phenyl]-oxy]hexanoic acid methyl ester with 2-thienylcarbaldehyde according to general operating instructions 5.

MS (EI): 434 (molecular ion peak)

b) 6-[[1-(4-Methylphenyl)-2-(2-thienyl)-1H-benzimidazol-6-yl]oxy]hexanoic acid was produced by reaction of 6-[[1-(4-methylphenyl)-2-(2-thienyl)-1H-benzimidazol-6-yl]oxy]hexanoic acid methyl ester according to general operating instructions 4.

MS (EI): 420 (molecular ion peak)

EXAMPLE 29

Inhibition of Microglia Activation

For in vitro production of Aβ-activated microglia, primary rat microglia with synthetic Aβ-peptide are incubated:

For simulation of Aβ deposits, synthetic Aβ peptide is dried on 96-hole tissue culture plates. A peptide stock solution is diluted by 2 mg/ml of $H_2O$ 1:50 in $H_2O$. To coat the 96-hole plates, 30 μl of this dilute peptide solution/hole is used, and it is dried overnight at room temperature.

Primary rat microglia are harvested by mixed glia cultures, which were obtained from P3 rat brains. In the production of mixed glia cultures, the brains are taken from 3-day-old rats, and meninges are removed. The isolation of cells is achieved by trypsinization (0.25% trypsin solution, 15 minutes, 37° C.)). After undigested tissue fragments are separated with the aid of a 40 μm nylon mesh, the isolated cells are centrifuged off (800 rpm/10 min). The cell pellet is resuspended in the culture medium and moved into 100 ml tissue culture flasks (1 brain/tissue culture flask). The cultivation of the cells is carried out over a period of 5 to 7 days in Dulbeccos. Modified Eagle Medium (DMEM, with glutamine), supplemented with penicillin (50 U/ml), streptomycin (40 μg/ml) and 10% (v/v) fetal calf serum (FCS) at 37° C. and 5% $CO_2$. During this incubation, an adhesive cellular film is formed, which mainly consists of astrocytes. Microglia proliferate as non-adhesive or weakly adhesive cells on the latter and are harvested via shaking incubation (420 rpm, 1 hour).

To activate the microglia by Aβ-peptide, $2.5 \times 10^4$ microglia/hole are grown on the Aβ-coated tissue culture plates and incubated over a period of 7 days in DMEM (with glutamine), supplemented with penicillin (50 U/ml), streptomycin (40 μg/ml) and 10% (v/v) fetal calf serum (FCS) at 37° C. and 5% $CO_2$. On day 5, a compound according to the invention is added at various concentrations (0.1, 0.3, 1.3 and 10 μM).

To quantify the microglia reactivity, the metabolic activity is measured on cultivation day 7 via the reduction of MTS (3-(4,5-dimethylthiazol-2-yl)-5-(3-carboxymethoxyphenyl)-2-(sulfophenyl)-2H-tetrazolium), Owen's reagent, Baltrop, J. A. et al. Bioorg. & Med. Chem. Lett., 1, 6111 (1991)). The percentage of inhibition relates to a control that is treated only with DMSO. The compounds according to the invention inhibit the microglia activation.

EXAMPLE 30

Cerebral Brain Infarction in Rats (MCAO Model)

The compounds according to the invention were tested for in vivo activity in an animal model for cerebral ischemia (stroke), the MCAO (permanent middle cerebral artery occlusion) model. One-sided obstruction of the middle cerebral artery (MCA) triggers a brain infarction, which is caused by the fact that the corresponding area of the brain is undernourished with oxygen and nutrients. The result of this undernourishment is a pronounced cellular degeneration and, subsequently, a strong microglia activation. This microglia activation reaches its maximum only after several days, however, and can last for several weeks. To test the substances, the compounds according to the invention were administered intraperitoneally 1-6 days after occlusion. On day 7, the animals were perfused and sacrificed. The extent of the microglia activation was measured by a modified immunohistochemical method. Vibratom sections of fixed brains were incubated with antibodies that detect the CR3 complement receptor or the MHCII complex on activated microglia. The quantification of the primary antibody bond was carried out by an enzyme-coupled detection system. The treatment with the compounds according to the invention resulted in a reduction of microglia activation in the brain hemisphere affected by the brain infraction.

EXAMPLE 31

Inhibition of the TNFα Production and IL 12 Production in THP-1 Cells

The inhibition of the cytokine production is visualized, for example, by measuring TNFα and interleukin 12 in lipopolysaccharide (LPS)-stimulated THP-1 cells.

For this purpose, $2.5 \times 10^6$ THP-1 cells (American Type Culture Company, Rockville, Md.)/ml of RPMI 1640 medium (Life Technologies)/10% FCS (Life Technologies, Cat. No. 10270-106) are grown on 96-hole flat-bottomed cell culture plates (TPP, Product No. 9296) (100 μl/hole). The compounds according to the invention are added at various concentrations and pre-incubated for 30 minutes. The pre-dilution of the test substances was performed in the incubation medium. The addition of the test substances is carried out as a 2× concentrated substance solution (100 μl/hole). The stimulation of the cells was carried out overnight at 37° C. with 0.1 μg/ml of LPS (Sigma L2630, of *E. coli* Serotype 011.B4). Then, the medium was harvested, and the amount of TNFα or the amount of interleukin 12 was quantitatively determined. To measure the TNFα, a commercially available TNFα kit of the CIS Bio International Company was used (Product No. 62TNFPEB). The amount of interleukin 12 was implemented with the aid of the ORIGEN Technologies (IGEN International, Inc., Gaithersburg, Md.). The calculated IC50 value corresponds to the concentration of test substance that is required to reach a 50% inhibition of the maximum TNFα or interleukin 12 production.

The compounds according to the invention inhibit the TNFα production and interleukin 12 production in lipopolysaccharide (LPS)-stimulated THP-1 cells.

EXAMPLE 32

Inhibition of the IFNγ Production of Peripheral Mononuclear Blood Cells

To visualize the effect of the substances on T-cell activation, for example, the measurement of the IFNγ-secretion is used.

To isolate peripheral mononuclear cells, human whole blood was used (drawing of blood via Na-citrate S-monovettes "Coagulation 9 NC/10 ml"/Sarstedt). The build-up of the blood cells was accomplished with the aid of density gradient centrifuging: For this purpose, 15 ml of Histopaque 1077 (Sigma, Cat. No. H8880) in LEUCOSEP tubes (Greiner, Cat. No. 227290) is introduced and centrifuged for 30 seconds at 1000 g. Then, 15 ml of whole blood is added and centrifuged for 10 minutes at 1000 g. Finally, the upper plasma layer is pipetted off and the subjacent cell layer (peripheral mononuclear blood cells) is transferred in 15 ml sample tubes (Falcon) and then washed several times with 10 ml of HBSS (HANKS Balanced Solution) (without $Mg^{2+}$ and $Ca^{2+}$) Cat. No. 14175-53). Finally, the cell pellet is resuspended in culture medium RPMI 1640+25 mmol of Hepes (Life Technologies Cat. No. 52400-04110% FCS (Life Technologies, Cat. No. 10270-106), 0.4% penicillin-streptomycin solution (Life Technologies, Cat. No. 15140-106) ($1\times10^6$ cells/ml). In each case, 100 µl of cell suspension solution was dispersed on 96-hole flat-bottomed cell culture plates (TPP, Product No. 9296) and stimulated with 2.5 µg/ml of anti-CD3 antibody. The substances according to the invention were added at various concentrations and pre-incubated for 30 minutes. The stimulation of the cells was carried out over a period of 24 hours. Then the medium was harvested, and the amount of IFNγ was determined quantitatively. The amount of IFNγ was determined with the aid of ORIGEN Technologies (IGEN International, Inc., Gaithersburg, Md.). The calculated IC50 value corresponds to the concentration of test substance that is required to reach a 50% inhibition of the maximum IFNγ production.

The compounds according to the invention inhibit the INFγ production of peripheral mononuclear blood cells.

EXAMPLE 33

Inhibition of the TNFα and IL-12 HD Production of Peripheral Mononuclear Blood Cells The inhibition of the TNFα and IL-12 HD p70 production is visualized by, for example, measuring TNFα and IL-12 HD p70 in peripheral mononuclear blood cells that are stimulated with lipopolysaccharide (LPS) and interferon gamma (IFNγ).

To isolate peripheral mononuclear blood cells, human whole blood was used (drawing of blood via Na-Citrate S-monovettes "Coagulation 9 NC/10 ml"/Sarstedt). The build-up of the lymphocytes and monocytes was accomplished with the aid of the density gradient centrifuging: For this purpose, 15 ml of Histopaque-1077 (Sigma, Cat. No. H8880) is introduced into 50 ml LEUCOSEP tubes (Greiner, Cat. No. 227290) and forced downward by centrifuging for 30 seconds at 250 g by the frits that are contained in the tubes. Then, 20 ml of whole blood is added and centrifuged for 15 minutes at 800 g and at room temperature. After centrifuging, the supernatant (plasma and thrombocytes) is pipetted off and discarded, and the subjacent cell layer (lymphocytes and monocytes) is transferred into 50 ml centrifuging tubes (Falcon) and then washed 3× in culture medium VLE RPMI 1640 (Seromed, No. FG1415) (centrifuging in each case for 10 minutes at 250 g, room temperature). Finally, the cell pellet is resuspended in culture medium VLE RPMI 1640 (Seromed, No. FG1415), 10% FCS (Life Technologies, Cat. No. 16000-044, low endotoxin, heat-inactivated for 1 hour, 56° C.), 50 µg/ml of penicillin-streptomycin solution (Life Technologies, Cat. No. 15140-106) and set at $3\times10^6$ cells/ml after cell counting by means of trypan blue staining. In each case, 100 µl of cell suspension solution was dispersed on 96-hole flat-bottomed cell culture plates (Costar, Product No. 3599). In each case, 100 µl of 3×-concentrated stimulation solution (3 µg/ml of LPS of *E. coli* Serotype 0127:B8: Sigma, Cat. No. L-4516 and 300 ng/ml of IFNγ 1b, Imukin, Boehringer Ingelheim) was added to it. The substances according to the invention were added at various concentrations as 3×-concentrated substance solution (100 µl/well). The stimulation of the cells was carried out at 37° C. and 5% $CO_2$ over a period of 24 hours. Then, the cell culture supernatant was harvested, and the concentrations of TNFα and IL-12 HD p70 were determined by means of commercially available ELISA Kits of the BioSource International Company (TNF-α EASIA, Cat. No. KAC1752) and R & D Systems (Quantikine™ HS IL-12, Cat. No. HS 120).

The calculated $IC_{50}$ value corresponds to the concentration of test substance that is required to reach a 50% inhibition of the maximum TNFα- or interleukin 12 HD p70 production.

The compounds according to the invention inhibit the TNFα and IL-12 HD p70 production of peripheral mononuclear blood cells.

EXAMPLE 34

Induction of IL-10 Production of Peripheral Mononuclear Blood Cells

The induction of IL-10 production is visualized by, for example, measuring IL-10 in peripheral mononuclear blood cells that are stimulated in phtyohemagglutinin (PHA) or lipopolysaccharide (LPS).

To isolate peripheral mononuclear blood cells, human whole blood was used (drawing of blood via Na-Citrate S-monovettes "Coagulation 9 NC/10 ml"/Sarstedt). The build-up of the lymphocytes and monocytes was accomplished with the aid of the density gradient centrifuging: For this purpose, 15 ml of Histopaque-1077 (Sigma, Cat. No. H8880) in 50 ml LEUCOSEP tubes (Greiner, Cat. No. 227290) is introduced and forced downward by centrifuging for 30 seconds at 250 g by the frits that are contained in the tubes. Then, 20 ml of whole blood is added and centrifuged for 15 minutes at 800 g and at room temperature. After centrifuging, the supernatant (plasma and thrombocytes) is pipetted off and discarded, and the subjacent cell layer (lymphocytes and monocytes) in 50 ml centrifuging tubes (Falcon) is transferred and then washed 3× in culture medium VLE RPMI 1640 (Seromed, No. FG1415) (centrifuging in each case for 10 minutes at 250 g, room temperature). Finally, the cell pellet is resuspended in culture medium VLE RPMI 1640 (Seromed, No. FG1415), 10% FCS (Life Technologies, Cat. No. 16000-044, low endotoxin, heat-inactivated for 1 hour, 56° C.), 50 µg/ml of penicillin-streptomycin solution (Life Technologies, Cat. No. 15140-106) and set at $3\times10^6$ cells/ml after cell counting by means of trypan blue staining. In each case, 100 µl of cell suspension solution was dispersed on 96-hole flat-bottomed cell culture plates (Costar, Product No. 3599). In each case, 100 µl of 3×-concentrated stimulation solution (3 µg/ml of LPS of *E. coli* Serotype 0127:B8; Sigma, Cat. No. L-4516 or 300 µg/ml of PHA-L, Biochrom KG, Cat. No. M5030) was added to it. The substances according to the invention were added at various concentrations as 3×-concentrated substance solution (100 µl/well). The stimulation of the cells was carried out at 37° C. and 5% $CO_2$ over a period of 24 hours. Then, the cell culture supernatant was harvested, and IL-10 was determined quantitatively. The IL-10 concentration was determined by means of a commercially available ELISA Kit of the BioSource International Company (human IL-10, Cat. No. KHC0101C). The calculated $EC_{50}$ value corresponds to the concentration of test substance that is required to increase the IL-10 secretion by 50% of the maximum increase.

The compounds according to the invention increase the IL-10 production of peripheral mononuclear blood cells.

The entire disclosures of all applications, patents and publications, cited herein and of corresponding German Application No. 102 07 844.0, filed Feb. 15, 2002, and U.S. Provisional Application Ser. No. 60/357,834, filed Feb. 21, 2002 are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for treating a patient suffering from arthritis, allergic contact dermatitis, psoriasis, asthma, rheumatoid arthritis, or stroke, which method comprises administering to said patient an effective amount of a benzimidazole compound of formula I:

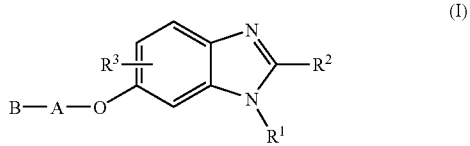

(I)

in which
R$^1$ is a phenyl group that is optionally substituted i) with up to three of the following substituents, independently of one another: F, Cl, Br, I, OH, OR$^4$, OCOR$^4$, SR$^4$, SOR$^4$, SO$_2$R$^4$, R$^4$, NH$_2$, NHR$^4$, and NR$^4$R$^{4'}$,
or ii) with two substituents at adjacent positions on the phenyl ring that together form an —O—CH$_2$—O—, —O—CH$_2$, CH$_2$—O— or —CH$_2$—CH$_2$—CH$_2$— group;
R$^2$ is a monocyclic or bicyclic 5- to 10-membered heteroaryl group with 1-2 heteroatoms, selected from N, S and O, which
i) optionally is substituted with up to two of the following substituents, independently of one another: F, Cl, Br, I, OH, OR$^4$, OCOR$^4$, COR$^4$, SR$^4$, SOR$^4$, SO$_2$R$^4$, and R$^4$,
or ii) optionally is substituted with two substituents at adjacent positions on the R$^2$ ring(s) that together form an —O—CH$_2$—O—, O—CH$_2$—, CH$_2$—O— or —CH$_2$—CH$_2$—CH$_2$— group;
R$^3$ is H, OH or O—C$_{1-6}$-alkyl;
R$^4$ and R$^{4'}$, independently of one another, are each C$_{1-4}$-perfluoroalkyl or C$_{1-6}$-alkyl;
A is a C$_{2-6}$-alkylene group, which optionally is substituted with =O, OH, O—C$_{1-3}$-alkyl, NH$_2$, NH—C$_{1-3}$-alkyl, NH—C$_{1-3}$-alkanoyl, N(C$_{1-3}$-alkyl)$_2$, or N(C$_{1-3}$-alkyl)(C$_{1-3}$-alkanoyl);
B is COOH, CONH$_2$, CONHNH$_2$, CONHR$^5$, or CONR$^5$R$^{5'}$, which in each case is bonded to a carbon atom of group A;
R$^5$ and R$^{5'}$, independently of one another, are in each case a radical, selected from: C$_{1-6}$-alkyl, C$_{2-6}$-alkenyl, C$_{2-6}$-alkinyl, wherein a C atom is optionally replaced by O, S, SO, SO$_2$, NH, N—C$_{1-3}$-alkyl or N—C$_{1-3}$-alkanoyl; C$_{0-3}$-alkanediyl-C$_{3-7}$-cycloalkyl, whereby in a five-membered cycloalkyl ring, a ring member is optionally a ring N or ring O, and in a six- or seven-membered cycloalkyl ring, one or two ring members in each case are optionally ring-N atoms and/or ring-O atoms, whereby the ring-N atoms are optionally substituted with C$_{1-3}$-alkyl or C$_{1-3}$-alkanoyl; C$_{0-3}$-alkanediyl-phenyl or C$_{0-3}$-alkanediyl-heteroaryl, whereby the heteroaryl group is five- or six-membered and contains one or two heteroatoms that are selected from N, S and O;
whereby all above-mentioned alkyl and cycloalkyl radicals are optionally substituted with up to two radicals that are selected from CF$_3$, C$_2$F$_5$, OH, O—C$_{1-3}$-alkyl, NH$_2$, NH—C$_{1-3}$-alkyl, NH—C$_{1-3}$-alkanoyl, N(C$_{1-3}$-alkyl)$_2$, N(C$_{1-3}$-alkyl)(C$_{1-3}$-alkanoyl), COOH, CONH$_2$, and COO—C$_{1-3}$-alkyl, and all above-mentioned phenyl and heteroaryl groups are optionally substituted with up to two radicals that are selected from F, Cl, Br, CH$_3$, C$_2$H$_5$, OH, OCH$_3$, OC$_2$H$_5$, NO$_2$, N(CH$_3$)$_2$, CF$_3$, C$_2$F$_5$, and SO$_2$NH$_2$;
or R$^5$ and R$^{5'}$ together with the N atom form a five- to seven-membered heterocyclic ring that optionally contains another N or O or S atom and is optionally substituted with C$_{1-4}$-alkyl, CO$_{0-2}$-alkanediyl-C$_{1-4}$-alkoxy, C$_{1-4}$-alkoxycarbonyl, aminocarbonyl, or phenyl;
or an optical or geometric isomer or tautomer form thereof, or a pharmaceutically acceptable salt thereof;
whereby the following compounds are excluded:
6-[[1-Phenyl-2-(pyridin-4-yl)-1H-benzim-idazol-6-yl]oxy]hexanoic acid, and
6-[[1-phenyl-2-(benzothien-2-yl)-1H-benzimi-dazol-6-yl]oxy]hexanoic acid.

2. The method according to claim 1, wherein said patient is suffering from arthritis.

3. The method according to claim 1, wherein said patient is suffering from allergic contact dermatitis.

4. The method according to claim 1, wherein said patient is suffering from psoriasis.

5. The method according to claim 1, wherein said patient is suffering from asthma.

6. A method according to claim 1, wherein R$^1$ is a phenyl group that optionally is substituted with up to two of the following substituents, independently of one another: F, Cl, OH, OR$^4$, OCOR$^4$, SR$_4$, and R$_4$, or two substituents at adjacent positions on the R$^1$ phenyl ring together form an —O—CH$_2$—O— or —CH$_2$—CH$_2$—CH$_2$— group.

7. A method according to claim 1, wherein R$^2$ is a monocyclic 5- to 6-membered heteroaryl group with 1-2 heteroatoms selected from N, S and O, which optionally is independently substituted with up to two of the following substituents: F, Cl, OR$^4$, OCOR$^4$, SR$^4$, SOR$^4$, SO$_2$R$^4$, and R$^4$, or two substituents at adjacent positions on the R$^2$ ring(s) together form an —O—CH$_2$—O— or —CH$_2$—CH$_2$—CH$_2$— group.

8. A method according to claim 1, wherein R$^3$ is H.

9. A method according to claim 1, wherein R$^4$ and R$^{4'}$, independently of one another, are C$_{1-2}$ perfluoroalkyl or C$_{1-4}$ alkyl.

10. A method according to claim 1, wherein R$^5$ and R$^{5'}$, independently of one another, are C$_{1-6}$-alkyl wherein a C atom is optionally replaced by O, S, SO, or SO$_2$; —C$_{3-5}$-cycloalkyl-C$_{0-3}$-alkylene, wherein in a five-membered cycloalkyl ring, a ring member is optionally a ring N or ring O and the ring N atom is optionally substituted with C$_{1-3}$-alkyl or C$_{1-3}$-alkanoyl; or C$_{0-2}$-alkylene-(5- to 6-membered heteroaryl with 1-2 heteroatoms selected from N, S and O), whereby the above-mentioned alkyl and cycloalkyl radicals are each optionally substituted with CF$_3$, OH, NH$_2$, NHC$_{1-3}$ alkyl, NHC$_{1-3}$ alkanoyl, N(C$_{1-3}$ alkyl)$_2$, N(C$_{1-3}$ alkyl)(C$_{1-3}$ alkanoyl), COOH, or CONH$_2$, and the above-mentioned heteroaryl group is optionally substituted with one or two substituents selected from F, Cl, CH$_3$, C$_2$H$_5$, OCH$_3$, OC$_2$H$_5$, CF$_3$, and C$_2$F$_5$,
or R$^5$ and R$^{5'}$ together with the nitrogen atom form a 5- to 7-membered heterocyclic compound, which optionally contains another oxygen, nitrogen or sulfur atom and is optionally substituted with $C_{1-4}$-alkyl or $C_{1-4}$-alkoxy-$C_{0-2}$-alkyl.

11. A method according to claim 1, wherein A is straight-chain $C_{3-6}$-alkylene.

12. A method according to claim 1, wherein B is COOH or $CONH_2$, in each case bonded to a carbon atom of group A.

13. A method according to claim 1, wherein said compound is:

6-[[1-(4-methylphenyl)-2-(3-pyridinyl)-1H-benzimidazol-6-yl]oxy]hexanoic acid or a pharmaceutically acceptable salt thereof;
  5-[[1-(4-methylphenyl)-2-(3-pyridinyl)-1H-benzimidazol-6-yl]oxy]pentanoic acid or a pharmaceutically acceptable salt thereof;
  4-[[1-(4-methylphenyl)-2-(3-pyridinyl)-1H-benzimidazol-6-yl]oxy]butyric acid or a pharmaceutically acceptable salt thereof;
  5-[[1-(4-methylphenyl)-2-(4-pyridinyl)-1H-benzimidazol-6-yl]oxy]hexanoic acid or a pharmaceutically acceptable salt thereof;
  6-[[1-(4-methylphenyl)-2-(3-thienyl)-1H-benzimidazol-6-yl]oxy]hexanoic acid or a pharmaceutically acceptable salt thereof;
  5-[[1-(4-methylphenyl)-2-(3-thienyl)-1H-benzimidazol-6-yl]oxy]pentanoic acid or a pharmaceutically acceptable salt thereof;
  4-[[1-(4-methylphenyl)-2-(3-thienyl)-1H-benzimidazol-6-yl]oxy]butyric acid or a pharmaceutically acceptable salt thereof;
  5-[[1-phenyl-2-(3-thienyl)-1H-benzimidazol-6-yl]oxy]pentanoic acid or a pharmaceutically acceptable salt thereof;
  4-[[1-phenyl-2-(3-thienyl)-1H-benzimidazol-6-yl]oxy]butyric acid or a pharmaceutically acceptable salt thereof;
  6-[[1-phenyl-2-(3-thienyl)-1H-benzimidazol-6-yl]oxy]hexanoic acid or a pharmaceutically acceptable salt thereof;
  6-[[1-(4-fluorophenyl)-2-(3-thienyl)-1H-benzimidazol-6-yl]oxy]hexanoic acid or a pharmaceutically acceptable salt thereof;
  5-[[1-(4-fluorophenyl)-2-(3-thienyl)-1H-benzimidazol-6-yl]oxy]pentanoic acid or a pharmaceutically acceptable salt thereof;
  6-[[1-(4-fluorophenyl)-2-(3-pyridinyl)-1H-benzimidazol-6-yl]oxy]hexanoic acid or a pharmaceutically acceptable salt thereof;
  5-[[1-(4-fluorophenyl)-2-(3-pyridinyl)-1H-benzimidazol-6-yl]oxy]pentanoic acid or a pharmaceutically acceptable salt thereof;
  5-[[1-phenyl-2-(3-pyridinyl)-1H-benzimidazol-6-yl]oxy]pentanoic acid or a pharmaceutically acceptable salt thereof;
  4-[[1-phenyl-2-(3-pyridinyl)-1H-benzimidazol-6-yl]oxy]butyric acid or a pharmaceutically acceptable salt thereof;
  6-[[1-phenyl-2-(3-pyridinyl)-1H-benzimidazol-6-yl]oxy]hexanoic acid or a pharmaceutically acceptable salt thereof;
  N-(3-methoxypropyl)-6-[[1-(4-methylphenyl)-2-(3-pyridinyl)-1H-benzimidazol-6-yl]oxy]hexanamide or a pharmaceutically acceptable salt thereof;
  6-[[1-(4-methylphenyl)-2-(3-pyridinyl)-1H-benzimidazol-6-yl]oxy]-1-morpholin-1-ylhexan-1-one or a pharmaceutically acceptable salt thereof;
  N-methyl-6-[[1-(4-methylphenyl)-2-(3-pyridinyl)-1H-benzimidazol-6-yl]oxy]hexanamide or a pharmaceutically acceptable salt thereof;
  N,N-dimethyl-6-[[1-(4-methyphenyl)-2-(3-pyridinyl)-1H-benzimidazol-6-yl]oxy ]hexanamide or a pharmaceutically acceptable salt thereof;
  6-[[1-(4-methylphenyl)-2-(3-pyridinyl)-1H-benzimidazol-6-yl]oxy]hexanamide or a pharmaceutically acceptable salt thereof;
  N-cyclopropyl-6-[[1-(4-methylphenyl)-2-(3-thienyl)-1H-benzimidazol-6-yl]oxy]hexanamide or a pharmaceutically acceptable salt thereof;
  N-methyl-6-[[1-(4-methylphenyl)-2-(3-thienyl)-1H-benzimidazol-6-yl]oxy]hexanamide or a pharmaceutically acceptable salt thereof;
  N-(2-methoxyethyl)-5-[[1-(4-methylphenyl)-2-(3-pyridinyl)-1H-benzimidazol-6-yl]oxy]pentanamide or a pharmaceutically acceptable salt thereof;
  N,N-dimethyl-5-[[1-(4-methylphenyl)-2-(3-pyridinyl)-1H-benzimidazol-6-yl]oxy]pentanamide or a pharmaceutically acceptable salt thereof;
  5-[[1-(4-methylphenyl)-2-(3-pyridinyl)-1H-benzimidazol-6-yl]oxy]pentanamide or a pharmaceutically acceptable salt thereof; or
  6-[[1-(4-methylphenyl)-2-(2-thienyl)-1H-benzimidazol-6-yl]oxy]hexanoic acid or a pharmaceutically acceptable salt thereof.

14. A method according to claim 13 wherein said compound is:

6-[[1-(4-methylphenyl)-2-(3-pyridinyl)-1H-benzimidazol-6-yl]oxy]hexanoic acid or a pharmaceutically acceptable salt thereof;
  5-[[1-(4-methylphenyl)-2-(3-pyridinyl)-1H-benzimidazol-6-yl]oxy]pentanoic acid or a pharmaceutically acceptable salt thereof;
  4-[[1-(4-methylphenyl)-2-(3-pyridinyl)-1H-benzimidazol-6-yl]oxy]butyric acid or a pharmaceutically acceptable salt thereof;
  5-[[1-(4-methylphenyl)-2-(4-pyridinyl)-1H-benzimidazol-6-yl]oxy]hexanoic acid or a pharmaceutically acceptable salt thereof;
  6-[[1-(4-fluorophenyl)-2-(3-pyridinyl)-1H-benzimidazol-6-yl]oxy]hexanoic acid or a pharmaceutically acceptable salt thereof;
  5-[[1-(4-fluorophenyl)-2-(3-pyridinyl)-1H-benzimidazol-6-yl]oxy]pentanoic acid or a pharmaceutically acceptable salt thereof;
  5-[[1-phenyl-2-(3-pyridinyl)-1H-benzimidazol-6-yl]oxy]pentanoic acid or a pharmaceutically acceptable salt thereof;
  4-[[1-phenyl-2-(3-pyridinyl)-1H-benzimidazol-6-yl]oxy]butyric acid or a pharmaceutically acceptable salt thereof;
  6-[[1-phenyl-2-(3-pyridinyl)-1H-benzimidazol-6-yl]oxy]hexanoic acid or a pharmaceutically acceptable salt thereof;
  N-(3-methoxypropyl)-6-[[1-(4-methylphenyl)-2-(3-pyridinyl)-1H-benzimidazol-6-yl]oxy]hexanamide or a pharmaceutically acceptable salt thereof;
  6-[[1-(4-methylphenyl)-2-(3-pyridinyl)-1H-benzimidazol-6-yl]oxy]-1-morpholin-1-ylhexan-1-one or a pharmaceutically acceptable salt thereof;
  N-methyl-6-[[1-(4-methylphenyl)-2-(3-pyridinyl)-1H-benzimidazol-6-yl]oxy]hexanamide or a pharmaceutically acceptable salt thereof;

N,N-dimethyl-6-[[1-(4-methyphenyl)-2-(3-pyridinyl)-1H-benzimidazol-6-yl]oxy]hexanamide or a pharmaceutically acceptable salt thereof;

6-[[1-(4-methylphenyl)-2-(3-pyridinyl)-1H-benzimidazol-6-yl]oxy]hexanoic acid or a pharmaceutically acceptable salt thereof;

N-(2-methoxyethyl)-5-[[1-(4-methylphenyl)-2-(3-pyridinyl)-1H-benzimidazol-6-yl]oxy]pentanamide or a pharmaceutically acceptable salt thereof;

N,N-dimethyl-5-[[1-(4-methyphenyl)-2-(3-pyridinyl)-1H-benzimidazol-6-yl]oxy]pentanamide or a pharmaceutically acceptable salt thereof; or 5-[[1-(4-methylphenyl)-2-(3-pyridinyl)-1H-benzimidazol-6-yl]oxy]pentanamide or a pharmaceutically acceptable salt thereof.

15. A method according to claim 13 wherein said compound is:

6-[[1-(4-methylphenyl)-2-(3-thienyl)-1H-benzimidazol-6-yl]oxy]hexanoic acid or a pharmaceutically acceptable salt thereof;

5-[[1-(4-methylphenyl)-2-(3-thienyl)-1H-benzimidazol-6-yl]oxy]pentanoic acid or a pharmaceutically acceptable salt thereof;

4-[[1-(4-methylphenyl)-2-(3-thienyl)-1H-benzimidazol-6-yl]oxy]butyric acid or a pharmaceutically acceptable salt thereof;

5-[[1-phenyl-2-(3-thienyl)-1H-benzimidazol-6-yl]oxy]pentanoic acid or a pharmaceutically acceptable salt thereof;

4-[[1-phenyl-2-(3-thienyl)-1H-benzimidazol-6-yl]oxy]butyric acid or a pharmaceutically acceptable salt thereof;

6-[[1-phenyl-2-(3-thienyl)-1H-benzimidazol-6-yl]oxy]hexanoic acid or a pharmaceutically acceptable salt thereof;

6-[[1-(4-fluorophenyl)-2-(3-thienyl)-1H-benzimidazol-6-yl]oxy]hexanoic acid or a pharmaceutically acceptable salt thereof;

5-[[1-(4-fluorophenyl)-2-(3-thienyl)-1H-benzimidazol-6-yl]oxy]pentanoic acid or a pharmaceutically acceptable salt thereof;

N-cyclopropyl-6-[[1-(4-methylphenyl)-2-(3-thienyl)-1H-benzimidazol-6-yl]oxy]hexanamide or a pharmaceutically acceptable salt thereof;

N-methyl-6-[[1-(4-methylphenyl)-2-(3-thienyl)-1H-benzimidazol-6-yl]oxy]hexanamide or a pharmaceutically acceptable salt thereof;

6-[[1-(4-methylphenyl)-2-(2-thienyl)-1H-benzimidazol-6-yl]oxy]hexanoic acid or a pharmaceutically acceptable salt thereof.

16. A method according to claim 1, wherein $R^2$ is a monocyclic 5- to 6-membered heteroaryl group selected from pyrrolyl, thienyl, furanyl, imidazolyl, thiazolyl, isothiazolyl, oxazolyl, isoxazolyl, pyrazolyl, pyridyl, pyrimidinyl, pyrazinyl, pyridazinyl, indolyl, isoindolyl, benzothiophenyl, benzofuranyl, benzimidazolyl, indazolyl, quinolyl, isoquinolyl, phthalazinyl, quinazolinyl, cinnolinyl, quinoxalinyl and naphthyridinyl, which in each case is optionally independently substituted with up to two of the following substituents: F, Cl, $OR^4$, $OCOR^4$, $SR^4$, $SOR^4$, $SO_2R^4$, $R^4$ or two substituents at adjacent positions on the $R^2$ ring(s) together form an —O—$CH_2$—O— or —$CH_2$—$CH_2$—$CH_2$— group.

17. A method according to claim 3, wherein said patient is suffering from rheumatoid arthritis.

18. A method according to claim 1, wherein said patient is suffering from a stroke.

19. A method according to claim 13, wherein said patient is suffering from arthritis, allergic contact dermatitis, psoriasis, asthma, or rheumatoid arthritis.

20. A method according to claim 13, wherein said patient is suffering from a stroke.

21. A method according to claim 1, wherein $R^1$ is a phenyl group that optionally is substituted with up to two of the following substituents, independently of one another: F, Cl, OH, $OR^4$, $OCOR^4$, $SR_4$, and $R_4$, or two substituents at adjacent positions on the $R^1$ phenyl ring together form an —O—$CH_2$—O— or $CH_2$—$CH_2$—$CH_2$— group;

$R^2$ is a monocyclic 5- to 6-membered heteroaryl group with 1-2 heteroatoms selected from N, S and O, which optionally is independently substituted with up to two of the following substituents: F, Cl, $OR^4$, $OCOR^4$, $SR^4$, $SOR^4$, $SO_2R^4$, and $R^4$, or two substituents at adjacent positions on the $R^2$ ring(s) together form an —O—$CH_2$—O— or —$CH_2$—$CH_2$—$CH_2$— group;

$R^3$ is H;

$R^4$ and $R^{4'}$, independently of one another, are $C_{1-2}$ perfluoroalkyl or $C_{1-4}$ alkyl;

$R^5$ and $R^{5'}$, independently of one another, are $C_{1-6}$-alkyl wherein a C atom is optionally replaced by O, S, SO, or $SO_2$; —$C_{3-5}$-cycloalkyl-$C_{0-3}$-alkylene, wherein in a five-membered cycloalkyl ring, a ring member is optionally a ring N or ring O and the ring N atom is optionally substituted with $C_{1-3}$-alkyl or $C_{1-3}$-alkanoyl; or $C_{0-2}$-alkylene-(5- to 6-membered heteroaryl with 1-2 heteroatoms selected from N, S and O), whereby the above-mentioned alkyl and cycloalkyl radicals for $R^5$ and $R^{5'}$ are each optionally substituted with $CF_3$, OH, $NH_2$, $NHC_{1-3}$ alkyl, $NHC_{1-3}$ alkanoyl, $N(C_{1-3}$ alkyl)$_2$, $N(C_{1-3}$ alkyl)($C_{1-3}$ alkanoyl), COOH, or $CONH_2$, and the above-mentioned heteroaryl group for $R^5$ and $R^{5'}$ is optionally substituted with one or two substituents selected from F, Cl, $CH_3$, $C_2H_5$, $OCH_3$, $OC_2H_5$, $CF_3$, and $C_2F_5$, or $R^5$ and $R^{5'}$ together with the nitrogen atom form a 5- to 7-membered heterocyclic compound, which optionally contains another oxygen, nitrogen or sulfur atom and is optionally substituted with $C_{1-4}$-alkyl or $C_{1-4}$-alkoxy-$C_{0-2}$-alkyl;

A is straight-chain $C_{3-6}$-alkylene; and

B is COOH or $CONH_2$, in each case bonded to a carbon atom of group A.

* * * * *